United States Patent
Sundermann et al.

(10) Patent No.: US 6,710,080 B2
(45) Date of Patent: Mar. 23, 2004

(54) SUBSTITUTED 2-DIALKYLAMINOALKYLBIPHENYL DERIVATIVES

(75) Inventors: Bernd Sundermann, Aachen (DE); Babette-Yvonne Koegel, Langerwehe-Hamich (DE); Helmut Buschmann, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/071,229

(22) Filed: Feb. 11, 2002

(65) Prior Publication Data

US 2002/0198251 A1 Dec. 26, 2002

Related U.S. Application Data

(63) Continuation of application No. PCT/EP00/07095, filed on Jul. 25, 2000.

(30) Foreign Application Priority Data

Aug. 9, 1999 (DE) .......................................... 199 37 537

(51) Int. Cl.⁷ ....................... A61K 31/275; C07C 211/29
(52) U.S. Cl. ....................... 514/524; 514/650; 558/422; 564/337
(58) Field of Search .......................... 564/337; 558/422; 514/650, 524

(56) References Cited

U.S. PATENT DOCUMENTS

| 3,443,943 | A | 5/1969 | Rogers et al. |
| 4,315,926 | A | 2/1982 | Gschwend |
| 4,473,709 | A | 9/1984 | Montgomery et al. |
| 5,672,596 | A | 9/1997 | Wyvratt et al. |

FOREIGN PATENT DOCUMENTS

| WO | WO 9822433 | * 10/1998 |

OTHER PUBLICATIONS

Peter W. Jeffs, et al., "Post–Tyrosine Intermediates in the Biosynthesis of Mesembrine Alkaloids and Stereochemistry of Protonation at C–7 in the Formation of the Octahydroindole Skeleton" J.C.S. Chemistry Communications, 1976.
Kevin E. Cullen, et al., "Reactions of Diene–conjugated 1,3–Dipolar Intermediates: A Versatile and Efficient Route to Dibenz[c,e]azepines via Benzonitrile o–Arylbenzyl Ylides" J. Chem. Soc. Perkin Trans., 1993.
Moshe Weitzberg, et al., "Synthesis and Chemistry of Some Dibenz[c,e]azepines" American Chemistry Society, vol. 87, 1987.
Robert J. DeVita, et al., "A Potent, Orally Bioavaiable Benzazepinone Growth Hormone Secretagogue" J. Med. Chem., vol. 41, 1998, pp. 1716–1728.
Shigeru Kobayahi, et al., "Syntheses of Apogalanthamine Analogs as a–Adrenergic Blocking Agents" Chem. Pharm. Bulletin, vol. 25, 1977.
Chemical Database, Article No. XP–002150441.
Chemical Database, Article No. XP–002150442.
A. Misiorny, et al., "Chemistry and CNS–effects of 2–aminomethyl–2'–hydroxybiphenyls and 2–aminomethyl–2'3'–dihydroxybiphenyls" Acta Pharm. Suec., vol. 14, 1977, pp. 105–122.
Ingrid Pettersson, et al., "Structure–activity relationships for apomorphine congeners. Conformational energies vs. biological activities" Journal of Computer–Aided Molecular Design, vol. 1, 1987, pp. 143–152.
W. Bersch, et al., "o–[o–(Dimethylaminomethyl)–phenyl] benzaldehyd" Archives of Pharm., vol. 44, 1950, pp. 91–94.
W. Bersch, et al., "Phenanthrenbildung durch Hofmann–Abbau" Archives of Pharm., Aug./Sep. 1957.
Gerard van Koten, et al., "Selective Formation of Biaryls via Interaction of Polynuclear Arylcopper Compounds with Copper(I) Trifluoromethanesulfonate [Copper(I) Triflate]" J. Org. Chem., vol. 42, No. 12, 1977.
St. Goldsschmidt, et al., "Diphenyl Derivatives I." Recueil, vol 67, 1948.
Jose Vicente, et al., "Gold in Organic Synthesis. Preparation of Symmetrical and Unsymmetrical Biaryls via C—C Coupling from cis–Diarylgold(III) Complexes" Organometallics, vol. 10, 1991, pp. 3380–3384.
Herbert O. House, et al., "The Solvolysis of Derivatives of 3–Azabicyclo[3.3.1]nonane" Department of Chemistry, MIT, vol. 31, 1966, pp. 3482–3489.
Arthur Lepley, et al., "Benzyne Addition to N,N–Dimethylbenzylamine" J. Org. Chem., vol. 36, No. 9, 1971.
N. Proskurnina, et al., "The Alkaloids of Galanthus Woronowi".
Shigeru Kobayashi, et al., "The Constitution of apoGalanthamine" School of Pharmacy, Aug. 27, 1956.
Chemical Abstracts, vol. 84, 1976, article No. 58806.
P. W. Jeffs et al., "Biosynthesis of Mesembrine and Related Alkaloids. The Amid Acid Precursors" Journal of American Chemistry Society, vol. 93, No. 15, Jul. 28, 1971.

* cited by examiner

*Primary Examiner*—Joseph K. McKane
*Assistant Examiner*—Kamal Saeed
(74) *Attorney, Agent, or Firm*—Crowell & Moring LLP

(57) ABSTRACT

Substituted 2-dialkylaminoalkylbiphenyl derivatives, processes for their preparation, pharmaceutical compositions comprising these compounds and methods using these compounds for the preparation of medicaments and for the treatment of diseases.

20 Claims, No Drawings

SUBSTITUTED 2-DIALKYLAMINOALKYLBIPHENYL DERIVATIVES

CROSS REFERENCE TO RELATED APPLICATIONS

The present application is a continuation of international patent application no. PCT/EP00/07095, filed Jul. 25, 2000, designating the United States of America, the entire disclosure of which is incorporated herein by reference. Priority is claimed based on Federal Republic of Germany patent application no. 199 37 537.2, filed Aug. 9, 1999.

BACKGROUND AND SUMMARY OF THE INVENTION

The invention relates to substituted 2-dialkylaminoalkylbiphenyl derivatives, processes for their preparation, medicaments comprising these compounds and the use of these compounds for the preparation of medicaments and methods of treatment using these components.

The treatment of chronic and non-chronic states of pain is of great importance in medicine. There is a worldwide demand for pain treatments which have a good efficacy. The urgent need for action in respect of patient-relevant and target-orientated treatment of chronic and non-chronic states of pain, this being understood as meaning successful and satisfactory pain treatment for the patient, is documented in the large number of scientific works which have recently appeared in the field of applied analgesia and fundamental research into nociception.

Conventional opioids, such as morphine, have a good action in the treatment of severe to very severe pain. However, their use is limited due to the known side effects, e.g. respiratory depressions, vomiting, sedation, constipation, addiction, dependency and development of tolerance. They can therefore be administered over a relatively long period of time or in relatively high dosages only with particular safety precautions, such as specific prescription instructions (Goodman, Gilman, The Pharmacological Basis of Therapeutics, Pergamon Press, New York 1990). Furthermore, they have a relatively low efficacy for some states of pain, in particular neuropathic pain.

An object of the instant invention was to provide analgesically active substances which are suitable for treatment of pain. Furthermore, these substances should have as few as possible of the side effects of opioid analgesics, such as nausea, vomiting, dependency, respiratory depression or constipation. Further objects are to provide active compounds for treatment of inflammatory and allergic reactions, depressions, drug and/or alcohol abuse, gastritis, diarrhoea, urinary incontinence, cardiovascular diseases, respiratory tract diseases, coughing, mental illnesses and/or epilepsy.

According to the invention, this is achieved by provision of new substituted 2-dialkylaminoalkylbiphenyl derivatives which are suitable for treatment of inflammatory and allergic reactions, depressions, drug and/or alcohol abuse, gastritis, diarrhoea, urinary incontinence, cardiovascular diseases, respiratory tract diseases, coughing, mental illnesses and/or epilepsy and which moreover have a pronounced analgesic action.

DETAILED DESCRIPTION OF THE INVENTION

The invention therefore provides substituted 2-dialkylaminoalkylbiphenyl derivatives of the general formula I

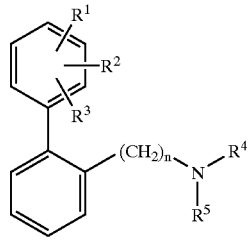

I

Wherein n is 1 or 2, the radicals $R^1$, $R^2$, $R^3$, which are identical or different, represent H, F, Cl, Br, CN, $NO_2$, CHO, $SO_2CH_3$, $SO_2CF_3$, $OR^6$, $NR^6R^7$, a $C_{1-6}$-alkyl, preferably a $C_{1-3}$-alkyl, an aryl, an acetyl, an acetamidyl or a benzoyl radical, or represent an aryl radical bonded via a $C_{1-6}$-alkylene group, preferably an aryl radical bonded via a $C_{1-3}$-alkylene group;

or $R^1$ and $R^2$ together in each case denote the group $OCH_2O$, $OCH_2CH_2O$, CH=CHO, CH=C($CH_3$)O or CH=CHNH;

the radicals $R^4$, $R^5$, which are identical or different, represent H, or represent a $C_{1-6}$-alkyl radical, preferably a $C_{1-3}$-alkyl radical;

the radicals $R^6$, $R^7$, which are identical or different, represent H, a $C_{1-6}$-alkyl, preferably a $C_{1-3}$-alkyl, or an aryl radical, or represent an aryl radical bonded via a $C_{1-6}$-alkylene group, preferably an aryl radical bonded via a $C_{1-3}$-alkylene group, in the form of their bases and/or salts of physiologically tolerated acids.

However, the compounds

2'-dimethylaminomethylbiphenyl-2-carbaldehyde;
biphenyl-2-ylmethyldimethylamine;
2'-dimethylaminomethylbiphenyl-2-ol, and the corresponding hydrochloride;
(2',3'-dimethoxybiphenyl-2-ylmethyl)dimethylamine, and the corresponding hydrochloride and the corresponding hydrobromide;
(4'-methylbiphenyl-2-ylmethyl)-dimethylamine;
(2'-methylbiphenyl-2-ylmethyl)-dimethylamine;
4-chloro-2'-dimethylaminomethylbiphenyl-2-carbonitrile;
(2'-dimethylaminomethylbiphenyl-2-yl)methanol;
2'-dimethylaminomethylbiphenyl-2,3-diol, and the corresponding hydrobromide;
[2-(3',4'-dimethoxybiphenyl-2-yl)ethyl)]-dimethylamine, and the corresponding hydrochloride;
[2-(2',3'-dimethoxy-6'-methylbiphenyl-2-yl)ethyl)]-dimethylamine, and the corresponding hydrobromide; and
biphenyl-2-ylethyldimethylamine are excluded.

Alkyl radicals are understood as meaning hydrocarbons which may be substituted, preferably by halogen and/or a hydroxyl group, particularly preferably by fluorine and/or a hydroxyl group. If there are more than one substituent, the substituents can be identical or different. The alkyl radicals methyl, ethyl, propyl, 1-methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, $CHF_2$, $CF_3$ or $CH_2OH$ are preferred.

An aryl radical is understood as meaning phenyls or naphthyl radicals which may be substituted by an OH, a halogen, preferably F and/or Cl, a $CF_3$, a $C_{1-6}$-alkyl, a $C_{1-6}$-alkoxy, a $C_{1-7}$-cycloalkoxy, a $C_{3-7}$-cycloalkyl, a $C_{2-6}$-alkylene or a phenyl radical. The phenyl radicals can also be condensed with further rings.

The following substituted 2-dimethylaminoalkylbiphenyl derivatives are particularly preferred:

(3'-methoxybiphenyl-2-ylmethyl)dimethylamine and the corresponding hydrochloride;
(4'-chlorobiphenyl-2-ylmethyl)dimethylamine and the corresponding hydrochloride;
2'-dimethylaminomethylbiphenyl-3-ol and the corresponding hydrochloride;
(2'-methoxybiphenyl-2-ylmethyl)dimethylamine and the corresponding hydrochloride;
(3'-chlorobiphenyl-2-ylmethyl)dimethylamine and the corresponding hydrochloride;
(2'-fluorobiphenyl-2-ylmethyl)dimethylamine and the corresponding hydrochloride;
(3'-fluorobiphenyl-2-ylmethyl)dimethylamine and the corresponding hydrochloride;
(4'-fluorobiphenyl-2-ylmethyl)dimethylamine and the corresponding hydrochloride;
(3'-chloro-4'-fluorobiphenyl-2-ylmethyl)dimethylamine and the corresponding hydrochloride;
(3'-methoxybiphenyl-2-ylmethyl)dimethylamine and the corresponding hydrochloride;
dimethyl-[2-(2-methylbenzofuran-4-yl)benzyl]amine and the corresponding hydrochloride;
2'-dimethylaminomethylbiphenyl-2-carbaldehyde and the corresponding hydrochloride;
(3'-difluoromethylbiphenyl-2-ylmethyl)dimethylamine and the corresponding hydrochloride;
2'-dimethylaminomethylbiphenyl-3-carbaldehyde and the corresponding hydrochloride;
biphenyl-2-ylmethyldimethylamine and the corresponding hydrochloride;
(3',4'-dichlorobiphenyl-2-ylmethyl)dimethylamine and the corresponding hydrochloride;
(3',5'-dichlorobiphenyl-2-ylmethyl)dimethylamine and the corresponding hydrochloride;
dimethyl-(4'-nitro-3'-trifluoromethylbiphenyl-2-ylmethyl)-amine and the corresponding hydrochloride;
(3',4'-difluorobiphenyl-2-ylmethyl)dimethylamine and the corresponding hydrochloride;
(4'-fluoro-3'-trifluoromethylbiphenyl-2-ylmethyl)dimethyl-amine and the corresponding hydrochloride;
(4'-chloro-3'-methoxybiphenyl-2-ylmethyl)dimethylamine and the corresponding hydrochloride;
N-(2'-dimethylaminomethyl-3-trifluoromethoxybiphenyl-4-yl)acetamide and the corresponding hydrochloride;
(3'-isopropoxybiphenyl-2-ylmethyl)dimethylamine and the corresponding and the corresponding hydrochloride;
2'-(2-dimethylaminoethyl)biphenyl-3-ol and the corresponding hydrochloride;
4-chloro-2'-dimethylaminomethylbiphenyl-3-ol and the corresponding hydrochloride;
[2-(1H-indol-5-yl)benzyl]dimethylamine and the corresponding hydrochloride;
(4'-methanesulfonylbiphenyl-2-ylmethyl)dimethylamine and the corresponding hydrochloride;
(2',4'-dichlorobiphenyl-2-ylmethyl)dimethylamine and the corresponding hydrochloride;
(2',3'-difluorobiphenyl-2-ylmethyl)dimethylamine and the corresponding hydrochloride;
(2',5'-difluorobiphenyl-2-ylmethyl)dimethylamine and the corresponding hydrochloride;
(2-benzo[1,3]dioxol-5-ylbenzyl)dimethylamine and the corresponding hydrochloride;
1-[2'-(2-dimethylaminoethyl)biphenyl-3-yl]ethanone and the corresponding hydrochloride;
[2-(3',4'-dimethoxybiphenyl-2-yl)ethyl]dimethylamine and the corresponding hydrochloride;
[2-(3'-isopropoxybiphenyl-2-yl)ethyl]dimethylamine and the corresponding hydrochloride;
[2-(4'-chloro-3'-methoxybiphenyl-2-yl)ethyl]dimethylamine and the corresponding hydrochloride;
4-chloro-2'-(2-dimethylaminoethyl)biphenyl-3-ol and the corresponding hydrochloride;
dimethyl-(3'-nitrobiphenyl-2-ylmethyl)amine and the corresponding hydrochloride;
4-amino-2'-dimethylaminomethylbiphenyl-3-ol and the corresponding dihydrochloride;
(3',5'-difluorobiphenyl-2-ylmethyl) dimethylamine and the corresponding hydrochloride;
(2',5'-dimethoxybiphenyl-2-ylmethyl)dimethylamine and the corresponding hydrochloride;
2'-dimethylaminomethyl-5-trifluoromethoxybiphenyl-2-ylamine and the corresponding dihydrochloride;
N-(2'-dimethylaminomethyl-5-trifluoromethoxybiphenyl-2-yl)acetamide and the corresponding hydrochloride; and
3,5-dichloro-2'-dimethylaminomethyl-biphenyl-4-ylamine and the corresponding hydrochloride.

The invention also provides processes for the preparation of substituted 2-dialkylaminoalkylbiphenyl derivatives of the general formula I. The processes are characterized in that the compounds of the general formula II, wherein Y denotes Cl, Br or I and m denotes 0 or 1,

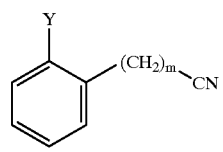

II are reduced in solution with a reducing agent, preferably lithium aluminium hydride and/or diisobutylaluminium hydride, to give rise to compounds of the general formula III, wherein n denotes 1 or 2,

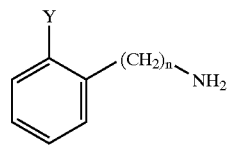

III and these are purified and isolated by conventional methods.

The compounds of the general formula III are then reacted with aliphatic $C_{1-6}$-aldehydes in the presence of a reducing agent, preferably formic acid and/or sodium borohydride, to give rise to compounds of the general formula IV

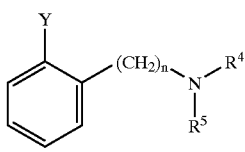

wherein $R^4$ and $R^5$ have the meaning according to the general formula I, and these are purified and isolated by conventional methods.

The compounds of the general formula IV are further converted by halogen-metal exchange, preferably with magnesium and/or butyllithium, and subsequent reaction with a boric acid ester, preferably a trialkyl borate, particularly preferably with a trimethyl borate, at temperatures of $\leq 0°$ C. to give rise to compounds of the general formula V,

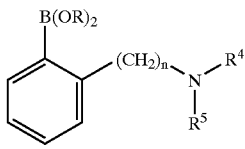

wherein R denotes a $C_{1-6}$-alkyl radical, and these are isolated and purified by conventional methods.

The compounds of the general formula V can be reacted with aqueous acids, preferably hydrochloric acid, to give rise to compounds of the general formula VI

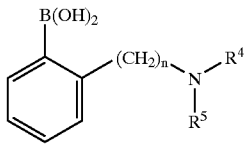

and these can be purified and isolated by conventional methods.

The compounds of the general formula V or VI are reacted in a transition metal-catalysed reaction, preferably in a reaction catalysed by palladium(0) compounds or by palladium(II) salts, particularly preferably by tetrakis (triphenylphosphine)palladium, bis(dibenzylideneacetone) palladium, elemental palladium on active charcoal, palladium(II) chloride and/or palladium(II) acetate, in an aliphatic ether, preferably 1,4-dioxane and tetrahydrofuran, or a hydrocarbon, preferably toluene or hexane, an alcohol, preferably ethanol or isopropanol, a chlorinated hydrocarbon, preferably chloroform or methylene chloride, in water or mixtures of these solvents at temperatures between 20 and 150° C. with compounds of the general formula VII

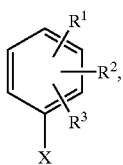

wherein X denotes Cl, Br, I or $OSO_2C_pF_{(2p+1)}$ and the radicals $R^1$ to $R^3$ have the meaning according to the general formula I, to give rise to compounds of the general formula I and these are purified and isolated by conventional methods.

Alternatively, the compounds of the general formula VIII or IX

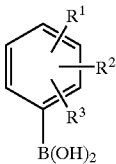

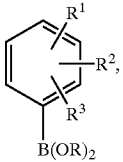

wherein $R^1$ to $R^3$ have the meaning according to the general formula I, are reacted in a transition metal-catalysed reaction, preferably in a reaction catalysed by palladium(0) compounds or by palladium(II) salts, particularly preferably by tetrakis(triphenylphosphine)palladium, bis (dibenzylideneacetone)palladium, elemental palladium on active charcoal, palladium(II) chloride and/or palladium(II) acetate, in an aliphatic ether, preferably 1,4-dioxane and tetrahydrofuran, or a hydrocarbon, preferably toluene or hexane, an alcohol, preferably ethanol or isopropanol, a chlorinated hydrocarbon, preferably chloroform or methylene chloride, in water or mixtures of these solvents at temperatures between 20 and 150° C. with compounds of the general formula III or IV to give rise to compounds of the general formula I and these are purified and isolated by conventional methods.

The compounds of the general formula I can be converted into their salts in the manner known to a skilled person in the art with physiologically tolerated acids, for example hydrochloric acid, hydrobromic acid, sulphuric acid, methanesulfonic acid, formic acid, acetic acid, oxalic acid, succinic acid, tartaric acid, mandelic acid, fumaric acid, lactic acid, citric acid, glutamic acid and/or aspartic acid. The salt formation is preferably carried out in a solvent, for example diethyl ether, diisopropyl ether, acetic acid alkyl esters, acetone and/or 2-butanone. Trimethylchlorosilane in aqueous solution is moreover suitable for preparation of the hydrochlorides.

The substituted 2-dialkylaminoalkylbiphenyl derivatives of the general formula I according to the invention are toxicologically acceptable and are therefore suitable pharmaceutical active compounds.

The invention therefore also provides medicaments or pharmaceutical compositions which comprise, as the active compound, at least one substituted 2-dialkylaminoalkylbiphenyl derivative of the general formula I in the form of its base and/or a salt of a physiologically tolerated acid and optionally further active compounds and auxiliary substances.

The medicaments are preferably employed for treatment or control of pain, inflammatory and allergic reactions, depressions, drug and alcohol abuse, gastritis, diarrhoea, urinary incontinence, cardiovascular diseases, respiratory tract diseases, coughing, mental illnesses and/or epilepsy.

The invention also additionally provides the use of at least one substituted 2-dialkylaminoalkylbiphenyl derivative of the general formula I in the form of its base and/or a salt of a physiologically tolerated acid for the preparation of a medicament and for treatment or control of pain, inflammatory and allergic reactions, depressions, drug and alcohol abuse, gastritis, diarrhoea, urinary incontinence, cardiovascular diseases, respiratory tract diseases, coughing, mental illnesses and/or epilepsy.

To prepare corresponding pharmaceutical formulations, in addition to at least one substituted 2-dimethylaminoalkylbiphenyl derivative of the general formula I, carrier materials, fillers, solvents, diluents, dyestuffs and/or binders are employed. The choice of auxiliary substances and the amounts thereof to be employed depend on whether the medicament is to be administered orally, intravenously, intraperitoneally, intradermally, intramuscularly, intranasally, buccally or locally, for example on infections on the skin, the mucous membranes and on the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Compounds of the general formula I according to the invention in a depot, in dissolved form or in a patch, optionally with the addition of agents which promote penetration through the skin, are suitable percutaneous administration formulations. Formulation forms which can be used orally or percutaneously can release the compounds of the general formula I according to the invention in a retarded manner.

The amount of active compound to be administered to the patient varies according to the weight of the patient, the mode of administration, the indication and the severity of the illness. Usually 0.5 to 500 mg/kg of at least one 2-dialkylaminoalkylbiphenyl derivative of the general formula I are administered.

EXAMPLES

The following examples serve to illustrate the invention, but do not limit the general inventive idea.

The yields of the compounds prepared are not optimized.

All temperatures are uncorrected.

The statement ether means diethyl ether.

Silica gel 60 (0.040–0.063 mm) from E. Merck, Darmstadt was employed as the stationary phase for the column chromatography.

The thin layer chromatography analyses were carried out with HPTLC precoated plates, silica gel 60 F 254 from E. Merck, Darmstadt.

The mixing ratios of the mobile phases for all the chromatography analyses are always stated in volume/volume.

Vol. % denotes percent by volume and wt. % denotes percent by weight.

Example 1
(3'-Methoxybiphenyl-2-ylmethyl)dimethylamine hydrochloride
1st Stage
3-Methoxybenzeneboronic acid 41.3 g (220 mmol) 3-bromoanisole were dissolved in 880 ml tetrahydrofuran and the solution was cooled to −70° C. in a cooling bath (ethanol/dry ice). 160 ml (250 mmol) butyllithium solution (1.6 M in hexane) were added dropwise under nitrogen such that the temperature did not rise above −60° C. After stirring at −70° C. for 1.5 hours, 75 ml (660 mmol) trimethyl borate were also added dropwise such that the temperature did not rise above −60° C. After stirring in the cold for a further hour, the mixture was warmed to 25° C. in the course of two hours, 720 ml hydrochloric acid (1 M) were added and the mixture was stirred at 25° C. for 15 hours.

For working up, the mixture was extracted three times with 300 ml ether each time, the organic phases were combined, washed with 100 ml each of water and saturated sodium chloride solution, dried over anhydrous magnesium sulfate and filtered and the filtrate was concentrated on a rotary evaporator (500–10 mbar). In this manner, 30.8 g 3-methoxybenzeneboronic acid (92.1% of theory) were obtained.

2nd Stage
(2-Bromobenzyl)dimethylamine 25.1 g (113 mmol) 2-bromobenzylamine hydrochloride were dissolved in 26 ml (678 mmol) formic acid and 52 ml (678 mmol) formaldehyde solution (36 wt. % in water) and the mixture was heated at 95° C. for 6 hours, while stirring. The solution was then cooled to 0° C. in an ice-bath and 90 g of cold potassium hydroxide solution (50 wt. %) were added. The mixture was extracted three times with 100 ml ether each time at 25° C., the organic phases were combined, a little active charcoal was added, the mixture was dried over anhydrous magnesium sulfate and filtered and the filtrate was concentrated on a rotary evaporator (500–10 mbar). 22.2 g (2-bromobenzyl)dimethylamine (91.9% of theory) were obtained in this manner.

3rd Stage
(3'-Methoxybiphenyl-2-ylmethyl)dimethylamine hydrochloride 1.13 g (7.43 mmol) 3-methoxybenzeneboronic acid, 1.67 g (7.78 mmol) (2-bromobenzyl)dimethylamine and 2.62 g (24.7 mmol) sodium carbonate were dissolved in a mixture of 50 ml toluene, 20 ml water and 10 ml ethanol. 175 mg tetrakis(triphenylphosphine)palladium(0) were added under nitrogen and the mixture was heated at 110° C. for 16 hours, while stirring.

For working up, 75 ml ether were added and the mixture was extracted three times with 75 ml of a potassium hydroxide solution (0.5 M) each time. The combined aqueous solutions were extracted with 30 ml ether, the combined organic phases were dried over anhydrous magnesium sulfate and filtered and the filtrate was concentrated on a rotary evaporator (500–10 mbar). 2.12 g of crude base (118% of theory) were added and were introduced on to a 3×25 cm column packed with silica gel. Elution with ether/n-hexane 1:1 (v:v) gave 0.61 g base, which was dissolved in 6.0 ml 2-butanone, and 25 µl (1.39 mmol) water and 350 µl (2.78 mmol) chlorotrimethylsilane were added in succession. The mixture was kept at 25° C. for 15 hours and the solid which had precipitated out was filtered off, washed with small portions of ether and dried to constant weight in an oil pump vacuum. 0.56 g (27.2% of theory) of (3'-methoxybiphenyl-2-ylmethyl)dimethylamine hydrochloride with a melting point of 144° C. was obtained in this manner.

Example 2
(4'-Chlorobiphenyl-2-ylmethyl)dimethylamine hydrochloride 0.88 g (5.65 mmol) 4-chlorobenzeneboronic acid, 1.27 g (5.93 mmol) of the (2-bromobenzyl)dimethylamine prepared according to example 1 (2nd stage) and 2.00 g (18.8 mmol) sodium carbonate were dissolved in a mixture of 39 ml toluene, 16 ml water and 8 ml ethanol. 133 mg tetrakis (triphenylphosphine)palladium(0) were added under nitrogen and the mixture was heated under reflux (bath temperature 110° C.) for 16 hours.

For working up, 65 ml ether were added and the mixture was extracted three times with 65 ml potassium hydroxide solution (0.5 M) each time. The combined aqueous solutions were re-extracted with 20 ml ether, the combined organic phases were dried over anhydrous magnesium sulfate and filtered and the filtrate was concentrated on a rotary evaporator (500–10 mbar). 1.30 g of crude base (93.8% of theory) were obtained and were introduced on to a 3×25 cm column packed with silica gel. Elution with ether/n-hexane 1:3 (v/v) gave 0.61 g of base, which was separated by HPLC for further purification. Separation conditions: mobile phase acetonitrile/water (80:20 (v/v) +0.5 vol. % isopropylamine), flow rate 10 ml/min, wavelength 254 nm, column Eurogel PRP 100 (manufacturer Knauer, 250×16 mm, with pre-column). 0.31 g of crude base was obtained, from which 0.33 g (20.7% of theory) (4'-chlorobiphenyl-2-ylmethyl)dimethylamine hydrochloride with a melting point of 232° C. was obtained according to example 1 (3rd stage) with chlorotrimethylsilane/water in 2-butanone.

Example 3
2'-Dimethylaminomethylbiphenyl-3-ol hydrochloride 0.70 g (2.52 mmol) of the (3'-methoxybiphenyl-2-ylmethyl)dimethylamine hydrochloride prepared according to example 1 (3rd stage) were dissolved in 10 ml water, the base was liberated with 10 ml water and 2 ml sodium hydroxide solution (32 wt. %), the mixture was extracted three times with 20 ml ether each time, the combined organic extracts were dried over anhydrous magnesium sulfate and filtered and the filtrate was concentrated on a rotary evaporator (500 to 10 mbar). 0.59 g (2.44 mmol) of this base was heated under reflux (bath temperature 145° C.) with 55 ml hydrogen bromide solution (48 wt. % in water) for two hours.

For working up, the mixture was poured into 600 ml sodium bicarbonate solution (1 M) (pH 7–8), and extracted three times with 100 ml ethyl acetate each time, the combined organic extracts were dried over anhydrous magnesium sulfate and filtered and the filtrate was concentrated on a rotary evaporator (500 to 10 mbar). 0.61 g crude base (109% of theory) was obtained and was introduced on to a 3×25 cm column packed with silica gel. Elution with ether gave 0.51 g of base, from which 0.51 g (79.7% of theory) 2'-dimethylaminomethylbiphenyl-3-ol hydrochloride with a melting point of 180° C. was obtained according to example 1 (3rd stage) with chlorotrimethylsilane/water in 2-butanone.

Example 4
(2'-Methoxybiphenyl-2-ylmethyl)dimethylamine hydrochloride 1.00 g (6.58 mmol) 4-methoxybenzeneboronic acid, 1.48 g (6.91 mmol) of the (2-bromobenzyl)dimethylamine prepared according to example 1 (2nd stage) and 2.32 g (21.9 mmol) sodium carbonate were dissolved in a mixture of 45 ml toluene, 18 ml water and 9 ml ethanol. 160 mg tetrakis(triphenylphosphine)palladium(0) were added under nitrogen and the mixture was heated under reflux (bath temperature 110° C.) for 16 hours.

For working up, 75 ml ether were added and the mixture was extracted three times with 75 ml potassium hydroxide solution (0.5 M) each time. The combined aqueous solutions were extracted with 20 ml ether, the combined organic phases were dried over anhydrous magnesium sulfate and filtered and the filtrate was concentrated on a rotary evaporator (500 to 10 mbar). 1.62 g of crude base (102% of theory) were obtained and were introduced on to a 3×25 cm column packed with silica gel. Elution with ether/n-hexane 1:2 (v/v) gave 0.64 g of base, from which 0.31 g (17.1% of theory) (2'-methoxybiphenyl-2-ylmethyl)dimethylamine hydrochloride with a melting point of 163° C. was obtained according to example 1 (3rd stage) with chlorotrimethylsilane/water in 2-butanone.

Example 5
(3'-Chlorobiphenyl-2-ylmethyl)dimethylamine hydrochloride 1.00 g (6.39 mmol) 3-chlorobenzeneboronic acid, 1.44 g (6.71 mmol) of the (2-bromobenzyl)dimethylamine prepared according to example 1 (2nd stage) and 2.26 g (21.3 mmol) sodium carbonate were dissolved in a mixture of 44 ml toluene, 17 ml water and 9 ml ethanol. 160 mg tetrakis(triphenylphosphine)palladium(0) were added under nitrogen and the mixture was heated under reflux (bath temperature 1 10° C.) for 16 hours.

For working up, 75 ml ether were added and the mixture was extracted three times with 75 ml potassium hydroxide solution (0.5 M) each time. The combined aqueous solutions were re-extracted with 20 ml ether, the combined organic phases were dried over anhydrous magnesium sulfate and filtered and the filtrate was concentrated on a rotary evaporator (500 to 10 mbar). 1.49 g of crude base (94.7% of theory) were obtained and were introduced on to a 3×25 cm column packed with silica gel. Elution with ether/n-hexane 1:1 (v/v) gave 0.62 g of base, from which a hydrochloride was precipitated according to example 1 (3rd stage) with chlorotrimethylsilane/water in 2-butanone. The base was liberated from this with 10 ml water and 2 ml sodium hydroxide solution (32 wt. %), the mixture was extracted three times with 20 ml ether each time, the combined organic extracts were dried over anhydrous magnesium sulfate and filtered and the filtrate was concentrated on a rotary evaporator (500 to 10 mbar). The resulting crude base was purified by HPLC. Separation conditions: mobile phase acetonitrile/water (80:20 (v/v) +0.5 vol. % isopropylamine), flow rate 10 ml/min, wavelength 254 nm, column Eurogel PRP 100 (manufacturer Knauer, 250×16 mm, with pre-column). 0.32 g of crude base was obtained, from which 0.29 g (16.3% of theory) (3'-chlorobiphenyl-2-ylmethyl)dimethylamine hydrochloride with a melting point of 169° C. was obtained according to example 1 (3rd stage) with chlorotrimethylsilane/water in 2-butanone.

Example 6
(2'-Fluorobiphenyl-2-ylmethyl)dimethylamine hydrochloride 1.02 g (7.27 mmol) 2-fluorobenzeneboronic acid, 1.63 g (7.63 mmol) of the (2-bromobenzyl)dimethylamine prepared according to example 1 (2nd stage) and 2.57 g (24.2 mmol) sodium carbonate were dissolved in a mixture of 50 ml toluene, 20 ml water and 10 ml ethanol. 172 mg tetrakis(triphenylphosphine)palladium(0) were added under nitrogen and the mixture was heated under reflux (bath temperature 110° C.) for 16 hours.

For working up, 80 ml ether were added and the mixture was extracted three times with 80 ml potassium hydroxide solution (0.5 M) each time. The combined aqueous solutions were re-extracted with 20 ml ether, the combined organic phases were dried over anhydrous magnesium sulfate and filtered and the filtrate was concentrated on a rotary evaporator (500 to 10 mbar). 1.73 g of crude base (104% of theory) were obtained and were introduced on to a 3×25 cm column packed with silica gel. Elution with ether/n-hexane 1:3 (v/v) gave 0.13 g of base, from which 0.10 g (4.7% of theory) (2'-fluorobiphenyl-2-ylmethyl)dimethylamine hydrochloride with a melting point of 184° C. was obtained according to example 1 (3rd stage) with chlorotrimethylsilane/water in 2-butanone.

Example 7
(3'-Fluorobiphenyl-2-ylmethyl)dimethylamine hydrochloride 1.03 g (7.39 mmol) 3-fluorobenzeneboronic acid, 1.05 g (4.93 mmol) of the (2-bromobenzyl)dimethylamine prepared according to example 1 (2nd stage) and 2.61 g (24.6 mmol) sodium carbonate were dissolved in a mixture of 50 ml toluene, 20 ml water and 10 ml ethanol. 175 mg tetrakis(triphenylphosphine)palladium(0) were added under nitrogen and the mixture was heated under reflux (bath temperature 110° C.) for 16 hours.

For working up, 80 ml ether were added and the mixture was extracted three times with 80 ml potassium hydroxide solution (0.5 M) each time. The combined aqueous solutions were re-extracted with 20 ml ether, the combined organic phases were dried over anhydrous magnesium sulfate and filtered and the filtrate was concentrated on a rotary evaporator (500–10 mbar). 1.38 g of crude base (122% of theory) were obtained and were introduced on to a 3×25 cm column packed with silica gel. Elution with ether/n-hexane 1:3 (v/v) gave 0.57 g of base, from which 0.53 g (41.9% of theory) (3'-fluorobiphenyl-2-ylmethyl)dimethylamine hydrochloride with a melting point of 183° C. was obtained according to example 1 (3rd stage) with chlorotrimethylsilane/water in 2-butanone.

Example 8
(4'-Fluorobiphenyl-2-ylmethyl)dimethylamine hydrochloride 1.00 g (7.15 mmol) 4-fluorobenzeneboronic acid, 1.02 g (4.76 mmol) of the (2-bromobenzyl)dimethylamine prepared according to example 1 (2nd stage) and 2.52 g (23.8 mmol) sodium carbonate were dissolved in a mixture of 50 ml toluene, 20 ml water and 10 ml ethanol. 170 mg tetrakis(triphenylphosphine)palladium(0) were added under nitrogen and the mixture was heated under reflux (bath temperature 110° C.) for 16 hours.

For working up, 80 ml ether were added and the mixture was extracted three times with 80 ml potassium hydroxide solution (0.5 M) each time. The combined aqueous solutions were re-extracted with 20 ml ether, the combined organic phases were dried over anhydrous magnesium sulfate and filtered and the filtrate was concentrated on a rotary evaporator (500–10 mbar). 1.21 g of crude base (111% of theory) were obtained and were introduced on to a 3×25 cm column packed with silica gel. Elution with ether/n-hexane 1:3 (v/v) gave 0.56 g of base, from which 0.56 g (44.0% of theory) (4'-fluorobiphenyl-2-ylmethyl)dimethylamine hydrochloride with a melting point of 222° C. was obtained according to example 1 (3rd stage) with chlorotrimethylsilane/water in 2-butanone.

Example 9
(3'-Chloro-4'-fluorobiphenyl-2-ylmethyl)dimethylamine hydrochloride 1.12 g (6.41 mmol) 3-chloro-4-fluorobenzeneboronic acid, 1.44 g (6.73 mmol) of the (2-bromobenzyl)dimethylamine prepared according to example 1 (2nd stage) and 2.26 g (21.4 mmol) sodium carbonate were dissolved in a mixture of 44 ml toluene, 18 ml water and 9 ml ethanol. 151 mg tetrakis(triphenylphosphine)palladium(0) were added under nitrogen and the mixture was heated under reflux (bath temperature 110° C.) for 16 hours.

For working up, 70 ml ether were added and the mixture was extracted three times with 70 ml potassium hydroxide solution (0.5 M) each time. The combined aqueous solutions were re-extracted with 20 ml ether, the combined organic phases were dried over anhydrous magnesium sulfate and filtered and the filtrate was concentrated on a rotary evaporator (500–10 mbar). 1.66 g of crude base (98.2% of theory) were obtained and were introduced on to a 3×25 cm column packed with silica gel. Elution with ether/n-hexane 1:1 (v/v) gave 0.66 g of base, which was purified by HPLC. Separation conditions: mobile phase acetonitrile/water (80:20 (v/v) +0.5 vol. % isopropylamine), flow rate 10 ml/min, wavelength 254 nm, column Eurogel PRP 100 (manufacturer Knauer, 250×4.6 mm, with pre-column). 0.37 g of crude base was obtained, from which 0.34 g (17.6% of theory) (3'-chloro-4'-fluorobiphenyl-2-ylmethyl)dimethylamine hydrochloride with a melting point of 205° C. was obtained according to example 1 (3rd stage) with chlorotrimethylsilane/water in 2-butanone.

Example 10
(3'-Methoxybiphenyl-2-ylethyl)dimethylamine hydrochloride

1st Stage
2-(2-Bromo-phenyl)-ethylamine 10.0 g (51.0 mmol) 2-bromophenylacetonitrile were dissolved in 80 ml ether and the solution was added dropwise to 5.81 g (153 mol) lithium aluminium hydride in 230 ml ether. The mixture was heated under reflux for three hours, while stirring, and, after cooling, 80 ml potassium hydroxide solution (10 wt. %) were slowly added dropwise, with vigorous stirring. After stirring overnight, the supernatant was decanted off, the residue was rinsed twice with 100 ml ether each time, the combined organic phases were dried over anhydrous magnesium sulfate and filtered and the filtrate was concentrated on a rotary evaporator (500–10 mbar). 9.48 g 2-(2-bromo-phenyl)-ethylamine (93% of theory) were obtained in this manner.

2nd Stage
[2-(2-Bromophenyl)ethyl]dimethylamine 9.42 g (47.3 mmol) 2-(2-bromophenyl)ethylamine were dissolved in 18 ml (473 mmol) formic acid and 36 ml (473 mmol) formaldehyde solution (36 wt. % in water) and the solution was heated at 95° C. under reflux for 6 hours, while stirring. This solution was then cooled to 0° C. in an ice-bath and 61 g cold potassium hydroxide solution (50 wt. %) were added. The mixture was extracted three times with 40 ml ether each time at 25° C., the organic phases were combined, a little active charcoal was added, the mixture was dried over magnesium sulfate and filtered and the filtrate was concentrated on a rotary evaporator (500–10 mbar). 11.3 g slightly contaminated [2-(2-bromophenyl)ethyl]dimethylamine (105% of theory) were obtained in this manner.

3rd Stage
(3'-Methoxybiphenyl-2-ylethyl)dimethylamine hydrochloride 2.0 g (13.2 mmol) of the 4-methoxybenzeneboronic acid prepared according to example 1 (1st stage), 3.15 g (13.8 mmol) [2-(2-bromophenyl)ethyl]dimethylamine from stage 1 and 4.66 g (43.8 mmol) sodium carbonate were dissolved in a mixture of 90 ml toluene, 36 ml water and 18 ml ethanol. 312 mg tetrakis(triphenylphosphine)palladium(0) were added under nitrogen and the mixture was heated under reflux (bath temperature 110° C.) for 16 hours.

For working up, 150 ml ether were added and the mixture was extracted three times with 150 ml potassium hydroxide solution (0.5 M) each time. The combined aqueous solutions were re-extracted with 50 ml ether, the combined organic phases were dried over anhydrous magnesium sulfate and filtered and the filtrate was concentrated on a rotary evaporator (500–10 mbar). 3.52 g of crude base (104% of theory) were obtained and were introduced on to a 4.5×33 cm column packed with silica gel. Elution with ether/n-hexane 1:1 (v/v) gave 2.24 g of base, which was purified by HPLC. Separation conditions: mobile phase acetonitrile/water (70:30 (v/v) +0.05 vol. % isopropylamine), flow rate 10 ml/min, wavelength 254 nm, column Eurogel PRP 100 (manufacturer Knauer, 250×16 mm, with pre-column). 0.96 g of crude base was obtained, from which 0.65 g (3'-methoxybiphenyl-2-ylethyl)dimethylamine hydrochloride (17.3% of theory) with a melting point of 143° C. was obtained according to example 1 (3rd stage) with chlorotrimethylsilane/water in 2-butanone.

Example 11
Dimethyl-[2-(2-methylbenzofuran-4-yl)benzyl]amine hydrochloride
1st Stage
2-(Dimethylaminomethyl)benzeneboronic acid 23.3 g (109 mmol) of the (2-bromobenzyl)dimethylamine prepared in example 1 (2nd stage) were dissolved in 400 ml tetrahydrofuran and the solution was cooled to −70° C. in a cooling bath (ethanol/dry ice). 78 ml (125 mmol) butyl-lithium solution (1.6 M in hexane) were added dropwise under nitrogen such that the temperature did not rise above −65° C. After the mixture had been stirred at −70° C. for 1.5 hours, 37 ml trimethyl borate were added dropwise such that the temperature did not rise above −60° C. After stirring in the cold for a further hour, the mixture was warmed to 25° C. in the course of two hours, 350 ml hydrochloric acid (1 M) were added and the mixture was stirred at 25° C. for 15 hours.

For working up, the mixture was neutralized with 10 ml sodium hydroxide solution (32 wt. %), rendered alkaline (pH approx. 9) with 3.5 g sodium carbonate and extracted three times with 150 ml ether each time, the organic phases were combined, dried over anhydrous magnesium sulfate and filtered and the filtrate was concentrated on a rotary evaporator (500–10 mbar). 9.29 g 2-(dimethylaminomethyl)benzeneboronic acid (47.7% of theory) were obtained in this manner.

2nd Stage
Dimethyl-[2-(2-methylbenzofuran-4-yl)benzyl]amine hydrochloride 1.00 g (5.59 mmol) 2-(dimethylaminomethyl)benzeneboronic acid from stage 1, 1.24 g (5.86 mmol) 4-bromo-2-methylbenzofuran and 1.97 g (18.6 mmol) sodium carbonate were dissolved in a mixture of 38 mol toluene, 15 ml water and 8 ml ethanol. 132 mg tetrakis(triphenylphosphine)palladium(0) were added under nitrogen and the mixture was heated under reflux (bath temperature 110° C.) for 16 hours.

For working up, 75 ml ether were added and the mixture was extracted three times with 75 ml potassium hydroxide solution (0.5 M) each time. The combined aqueous solutions were re-extracted with 20 ml ether, the combined organic phases were dried over anhydrous magnesium sulfate and filtered and the filtrate was concentrated on a rotary evaporator (500–10 mbar). 1.75 g of crude base (124% of theory) were obtained and were introduced on to a 3×25 cm column packed with silica gel. Elution with ether/n-hexane 1.3 (v:v) gave 0.78 g of base, from which 0.64 g (39.5% of theory) dimethyl-[2-(2-methylbenzofuran-4-yl)benzyl]amine hydrochloride with a melting point of 217° C. was obtained according to example 1 (3rd stage) with chlorotrimethylsilane/water in 2-butanone.

Example 12
2'-Dimethylaminomethylbiphenyl-2-carbaldehyde hydrochloride 1.20 g (7.97 mmol) 4-formylbenzeneboronic acid, 1.63 g (7.59 mmol) of the (2-bromobenzyl)dimethylamine prepared according to example 1 (2nd stage) and 2.68 g (25.3 mmol) sodium carbonate were dissolved in a mixture of 52 ml toluene, 21 ml water and 10 ml ethanol. 180 mg tetrakis(triphenylphosphine)palladium(0) were added under nitrogen and the mixture was heated under reflux (bath temperature 110° C.) for 16 hours.

For working up, 85 ml ether were added and the mixture was extracted three times with 85 ml potassium hydroxide solution (0.5 M) each time. The combined aqueous solutions were re-extracted with 20 ml ether, the combined organic phases were dried over anhydrous magnesium sulfate and filtered and the filtrate was concentrated on a rotary evaporator (500–10 mbar). 1.87 g of crude base (98.2% of theory) were obtained. The base was dissolved in 50 ml ether, the solution was extracted three times with 25 ml hydrochloric acid (5 wt. %) each time and the combined acid phases were washed with 10 ml ether and rendered alkaline (pH approx. 11) with 15 ml sodium hydroxide solution (32 wt. %). The mixture was extracted three times with 25 ml ether each time, the combined organic phases were dried over anhydrous magnesium sulfate and filtered and the filtrate was concentrated on a rotary evaporator (500–10 mbar). 1.28 g of crude base (70.3% of theory) were obtained and were introduced on to a 3×25 cm column packed with silica gel. Elution with ether/n-hexane 1:1 (v:v) gave 0.42 g of base, from which 0.43 g (20.5% of theory) 2'-dimethylaminomethylbiphenyl-2-carbaldehyde hydrochloride with a melting point of 230° C. was obtained according to example 1 (3rd stage) with chlorotrimethylsilane/water in 2-butanone.

Example 13
(3'-Difluoromethylbiphenyl-2-ylmethyl)dimethylamine hydrochloride 0.98 g (5.46 mmol) of the 2-(dimethylaminomethyl)benzeneboronic acid prepared according to example 11 (1st stage), 1.19 g (5.73 mmol) 1-bromo-3-difluoromethylbenzene and 1.93 g (18.2 mmol) sodium carbonate were dissolved in a mixture of 37 ml toluene, 15 ml water and 8 ml ethanol. 130 mg tetrakis(triphenylphosphine)palladium(0) were added under nitrogen and the mixture was heated under reflux (bath temperature 110° C.) for 16 hours.

For working up, 60 ml ether were added and the mixture was extracted three times with 60 ml potassium hydroxide solution (0.5 M) each time. The combined aqueous solutions were re-extracted with 20 ml ether, the combined organic phases were dried over anhydrous magnesium sulfate and filtered and the filtrate was concentrated on a rotary evaporator (500–10 mbar). 1.46 g of crude base (103% of theory) were obtained and were introduced on to a 3×25 cm column packed with silica gel. Elution with ether/n-hexane 1:3 (v/v) gave 0.79 g of base, from which 0.67 g (40.9% of theory) (3'-difluoromethylbiphenyl-2-ylmethyl)dimethylamine hydrochloride with a melting point of 147° C. was obtained according to example 1 (3rd stage) with chlorotrimethylsilane/water in 2-butanone.

Example 14
2'-Dimethylaminomethylbiphenyl-3-carbaldehyde hydrochloride 1.03 g (6.89 mmol) 3-formylbenzeneboronic acid, 1.40 g (6.56 mmol) of the (2-bromobenzyl)dimethylamine prepared according to example 1 (2nd stage) and 2.32 g (21.8 mmol) sodium carbonate were dissolved in a mixture of 45 ml toluene, 18 ml water and 9 ml ethanol. 156 mg tetrakis(triphenylphosphine)palladium(0) were added under nitrogen and the mixture was heated under reflux (bath temperature 110° C.) for 16 hours.

For working up, 75 ml ether were added and the mixture was extracted three times with 75 ml potassium hydroxide solution (0.5 M) each time. The combined aqueous solutions were re-extracted with 20 ml ether, the combined organic phases were dried over anhydrous magnesium sulfate and filtered and the filtrate was concentrated on a rotary evaporator (500–10 mbar). 1.66 g of crude base (100% of theory) were obtained. The base was dissolved in 50 ml ether, the solution was extracted three times with 25 ml hydrochloric acid (5 wt. %) each time and the combined acid phases were washed with 10 ml ether and rendered alkaline (pH approx. 11) with 15 ml sodium hydroxide solution (32 wt. %). the mixture was extracted three times with 25 ml ether each time, the combined organic phases were dried over anhydrous magnesium sulfate and filtered and the filtrate was concentrated on a rotary evaporator (500–10 mbar). 1.08 g of crude base (68.7% of theory) were obtained and were introduced on to a 3×25 cm column packed with silica gel. Elution with ether/n-hexane 1:3 (v:v) gave 0.40 g base, from which 0.31 g (17.3% of theory) 2'-dimethylaminomethylbiphenyl-3-carbaldehyde hydrochloride with a melting point of 185° C. was obtained according to example 1 (3rd stage) with chlorotrimethylsilane/water in 2-butanone.

Example 15
Biphenyl-2-ylmethyldimethylamine -bromobenzyl) dimethylamine hydrochloride 1.01 g (8.30 mmol) benzeneboronic acid, 1.69 g (7.90 mmol) of the (2-bromobenzyl)dimethylamine prepared according to example 1 (2nd stage) and 2.79 g (26.3 mmol) sodium carbonate were dissolved in a mixture of 54 ml toluene, 22 ml water and 11 ml ethanol. 187 mg tetrakis (triphenyl-phosphine)palladium(0) were added under nitrogen and the mixture was heated under reflux (bath temperature 110° C.) for 16 hours.

For working up, 90 ml ether were added and the mixture was extracted three times with 90 ml potassium hydroxide solution (0.5 M) each time. The combined aqueous solutions were re-extracted with 20 ml ether, the combined organic phases were dried over anhydrous magnesium sulfate and filtered and the filtrate was concentrated on a rotary evaporator (500–10 mbar). 1.64 g of crude base (93.3% of theory) were obtained and were introduced on to a 3×25 cm column packed with silica gel. Elution with ether/n-hexane 1:3 (v/v) gave 0.26 g of base, from which 0.28 g (14.2% of theory) biphenyl-2-ylmethyldimethylamine hydrochloride with a melting point of 189° C. was obtained according to example 1 (3rd stage) with chlorotrimethylsilane/water in 2-butanone.

Example 16
(3',4'-Dichlorobiphenyl-2-ylmethyl)dimethylamine hydrochloride 1.01 g (5.29 mmol) 3,4-dichlorobenzeneboronic acid, 1.19 g (5.56 mmol) of the (2-bromobenzyl)dimethylamine prepared according to example 1 (2nd stage) and 1.87 g (17.6 mmol) sodium carbonate were dissolved in a mixture of 36 ml toluene, 15 ml water and 7 ml ethanol. 125 mg tetrakis(triphenylphosphine)palladium(0) were added under nitrogen and the mixture was heated under reflux (bath temperature 110° C.) for 16 hours.

For working up, 60 ml ether were added and the mixture was extracted three times with 60 ml potassium hydroxide solution (0.5 M) each time. The combined aqueous solutions were re-extracted with 20 ml ether, the combined organic phases were dried over anhydrous magnesium sulfate and filtered and the filtrate was concentrated on a rotary evaporator (500–10 mbar). 1.43 g of crude base (96.5% of theory) were obtained and were introduced on to a 3×25 cm column packed with silica gel. Elution with ether/n-hexane 1:3 (v/v) gave 0.52 g of base, which was separated by HPLC for further purification. Separation conditions: mobile phase acetonitrile/water (90:10 (v/v) +0.05 vol. % isopropylamine), flow rate 10 ml/min, wavelength 254 nm, column Eurogel PRP 100 (manufacturer Knauer, 250×16 mm, with pre-column). 0.20 g of crude base was obtained, from which 0.19 g (11.4% of theory) (3',4'-dichlorobiphenyl-2-ylmethyl)dimethylamine hydrochloride with a melting point of 219° C. was obtained according to example 1 (3rd stage) with chlorotrimethylsilane/water in 2-butanone.

Example 17
(3',5'-Dichlorobiphenyl-2-ylmethyl)dimethylamine hydrochloride 0.89 g (4.66 mmol) 3,5-dichlorobenzeneboronic acid, 0.95 g (4.44 mmol) of the (2-bromobenzyl)dimethylamine prepared according to example 1 (2nd stage) and 1.57 g (14.8 mmol) sodium carbonate were dissolved in a mixture of 30 ml toluene, 12 ml water and 6 ml ethanol. 106 mg tetrakis(triphenylphosphine)palladium(0) were added under nitrogen and the mixture was heated under reflux (bath temperature 110° C.) for 16 hours.

For working up, 50 ml ether were added and the mixture was extracted three times with 50 ml potassium hydroxide solution (0.5 M) each time. The combined aqueous solutions were re-extracted with 20 ml ether, the combined organic phases were dried over anhydrous magnesium sulfate and filtered and the filtrate was concentrated on a rotary evaporator (500–10 mbar). 1.25 g of crude base (95.5% of theory) were obtained. The base was dissolved in 50 ml ether, the solution was extracted three times with 25 ml hydrochloric acid (5 wt. %) each time and the combined acid phases were washed with 10 ml ether and rendered alkaline (pH approx. 11) with 15 ml sodium hydroxide solution (32 wt. %). The mixture was extracted three times with 25 ml ether each time, the combined organic phases were dried over anhydrous magnesium sulfate and filtered and the filtrate was concentrated on a rotary evaporator (500–10 mbar). 0.46 g of crude base (37.3% of theory) was obtained and was introduced on to a 3×15 cm column packed with silica gel. Elution with ether/n-hexane 1:3 (v:v) gave 0.23 g of base, from which 0.20 g (14.9% of theory) (3',5'-dichlorobiphenyl-2-ylmethyl)dimethylamine hydrochloride with a melting point of 198° C. was obtained according to example 1 (3rd stage) with chlorotrimethylsilane/water in 2-butanone.

Example 18
Dimethyl-(4'-nitro-3'-trifluoromethylbiphenyl-2-ylmethyl)amine hydrochloride 1st Stage Dimethyl 2-(dimethylaminomethyl)benzeneboronate 20.2 g (94.2 mmol) of the (2-bromobenzyl) dimethylamine prepared according to example 1 (2nd stage) were dissolved in 350 ml tetrahydrofuran and the solution was cooled to −70° C. in a cooling bath (isopropanol/dry ice). 68 ml (108 mmol) butyllithium solution (1.6 M in hexane) were added dropwise under nitrogen such that the temperature did not rise above −60° C. After the mixture had been stirred at −70° C. for two hours, 32 ml (282 mmol) trimethyl borate were also added dropwise such that the temperature did not rise above −60° C. The mixture was warmed to 25° C. in the course of 15 hours and the solution was concentrated on a rotary evaporator (500–10 mbar) without heat being supplied. The residue was taken up in 200 ml n-hexane, the mixture was stirred for one hour and filtered over an inert gas frit under nitrogen and the filtrate was concentrated on a rotary evaporator (500–10 mbar) without heat being supplied. 12.0 g dimethyl 2-(dimethylaminomethyl)benzeneboronate (61.5% of theory) were obtained in this manner.

2nd Stage

Dimethyl-(4'-nitro-3'-trifluoromethylbiphenyl-2-ylmethyl) amine hydrochloride 1.84 g (8.89 mmol) of the dimethyl 2-(dimethylaminomethyl)-benzeneboronate prepared according to stage 1, 1.20 g (4.44 mmol) 5-bromo-2-nitrobenzotrifluoride and 1.57 g (14.8 mmol) sodium carbonate were dissolved in a mixture of 30 ml toluene, 12 ml water and 6 ml ethanol. 105 mg tetrakis(triphenylphosphine)palladium(0) were added under nitrogen and the mixture was heated under reflux (bath temperature 110° C.) for 16 hours.

For working up, 45 ml ether were added and the mixture was washed three times with 45 ml potassium hydroxide solution (0.5 M) each time. The organic solution was extracted three times with 17 ml hydrochloric acid (5 wt. %) each time and the combined acid phases were washed with 10 ml ether and rendered alkaline (pH approx. 12) with 10 ml sodium hydroxide solution (32 wt. %). The mixture was extracted three times with 20 ml ether each time, the combined organic phases were dried over anhydrous magnesium sulfate and filtered and the filtrate was concentrated on a rotary evaporator (500–10 mbar). 1.29 g of crude base (89.4% of theory) were obtained and were introduced on to a 3×15 cm column packed with silica gel. Elution with ether/n-hexane 1:10 (v:v) gave 1.05 g of base, from which 1.02 g (66.1% of theory) dimethyl-(4'-nitro-3'-trifluoromethylbiphenyl-2-ylmethyl)amine hydrochloride with a melting point above 240° C. were obtained according to example 1 (3rd stage) with chlorotrimethylsilane/water in 2-butanone.

Example 19

(3',4'-Difluorobiphenyl-2-ylmethyl)dimethylamine hydrochloride 1.01 g (4.87 mmol) of the dimethyl 2-(dimethylaminomethyl)-benzeneboronate prepared according to example 18 (1st stage), 1.88 g (9.75 mmol) 3,4-difluorobromobenzene and 1.72 g (16.2 mmol) sodium carbonate were dissolved in a mixture of 33 ml toluene, 13 ml water and 7 ml ethanol. 116 mg tetrakis(triphenylphosphine)palladium(0) were added under nitrogen and the mixture was heated under reflux (bath temperature 110° C.) for 16 hours.

For working up, 55 ml ether were added and the mixture was washed three times with 55 ml potassium hydroxide solution (0.5 M) each time. The organic solution was extracted three times with 22 ml hydrochloric acid (5 wt. %) each time and the combined acid phases were washed with 10 ml ether and rendered alkaline (pH approx. 12) with 13 ml sodium hydroxide solution (32 wt. %). The mixture was extracted three times with 20 ml ether each time, the combined organic phases were dried over anhydrous magnesium sulfate and filtered and the filtrate was concentrated on a rotary evaporator (500–10 mbar). 0.67 g of crude base (55.3% of theory) was obtained and was introduced on to a 3×15 cm column packed with silica gel. Elution with ether/n-hexane 1:10 (v:v) gave 0.47 g of base, from which 0.52 g (37.6% of theory) (3',4'-difluorobiphenyl-2-ylmethyl) dimethylamine hydrochloride with a melting point of 222° C. was obtained according to example 1 (3rd stage) with chlorotrimethylsilane/water in 2-butanone.

Example 20

(4'-Fluoro-3'-trifluoromethylbiphenyl-2-ylmethyl)dimethyl-amine hydrochloride 1.02 g (4.91 mmol) of the dimethyl 2-(dimethylaminomethyl)-benzeneboronate prepared according to example 18 (1st stage), 2.38 g (9.81 mmol) 5-bromo-2-fluorobenzotrifluoride and 1.73 g (16.3 mmol) sodium carbonate were dissolved in a mixture of 34 ml toluene, 14 ml water and 7 ml ethanol. 117 mg tetrakis(triphenylphosphine)palladium(0) were added under nitrogen and the mixture was heated under reflux (bath temperature 110° C.) for 16 hours.

For working up, 55 ml ether were added and the mixture was washed three times with 55 ml potassium hydroxide solution (0.5 M) each time. The organic solution was extracted three times with 22 ml hydrochloric acid (5 wt. %) each time and the combined acid phases were washed with 10 ml ether and rendered alkaline (pH approx. 12) with 13 ml sodium hydroxide solution (32 wt. %). The mixture was extracted three times with 20 ml ether each time, the combined organic phases were dried over anhydrous magnesium sulfate and filtered and the filtrate was concentrated on a rotary evaporator (500–10 mbar). 0.55 g of crude base (37.5% of theory) was obtained and was introduced on to a 3×15 cm column packed with silica gel. Elution with ether/n-hexane 1:10 (v:v) gave 0.39 g of base, from which 0.37 g (22.8% of theory) 4'-fluoro-3'-trifluoromethylbiphenyl-2-ylmethyl)dimethyl-amine hydrochloride with a melting point of 180° C. was obtained according to example 1 (3rd stage) with chlorotrimethylsilane/water in 2-butanone.

Example 21

(4'-Chloro-3'-methoxybiphenyl-2-ylmethyl)dimethylamine hydrochloride 1.52 g (4.87 mmol) of the dimethyl 2-(dimethylaminomethyl)-benzeneboronate prepared according to example 18 (1st stage), 1.08 g (4.88 mmol) 5-bromo-2-chloromethoxybenzene and 1.72 g (16.3 mmol) sodium carbonate were dissolved in a mixture of 33 ml toluene, 13 ml water and 7 ml ethanol. 116 mg tetrakis(triphenylphosphine)palladium(0) were added under nitrogen and the mixture was heated under reflux (bath temperature 110° C.) for 16 hours.

For working up, 55 ml ether were added and the mixture was washed three times with 55 ml potassium hydroxide solution (0.5 M) each time. The organic solution was extracted three times with 22 ml hydrochloric acid (5 wt. %) each time and the combined acid phases were washed with 10 ml ether and rendered alkaline (pH approx. 12) with 13 ml sodium hydroxide solution (32 wt. %). The mixture was extracted three times with 20 ml ether each time, the combined organic phases were dried over anhydrous magnesium sulfate and filtered and the filtrate was concentrated on a rotary evaporator (500–10 mbar). 1.26 g of crude base (93.3% of theory) were obtained and were introduced on to a 3×15 cm column packed with silica gel. Elution with ether/n-hexane 1:20 (v:v) gave 0.44 g of base, from which 0.46 g (29.9% of theory) (4'-chloro-3'-methoxybiphenyl-2-ylmethyl)dimethylamine hydrochloride with a melting point of 218° C. was obtained according to example 1 (3rd stage) with chlorotrimethylsilane/water in 2-butanone.

Example 22
N-(2'-Dimethylaminomethyl-3-trifluoromethoxybiphenyl-4-yl)acetamide hydrochloride 1.55 g (7.48 mmol) of the dimethyl 2-(dimethylaminomethyl)-benzeneboronate prepared according to example 18 (1st stage), 1.49 g (4.99 mmol) 4-bromo-2-(trifluoromethoxy)acetamide and 1.76 g (16.6 mmol) sodium carbonate were dissolved in a mixture of 34 ml toluene, 14 ml water and 7 ml ethanol. 118 mg tetrakis (triphenylphosphine)palladium(0) were added under nitrogen and the mixture was heated under reflux (bath temperature 110° C.) for 16 hours.

For working up, 55 ml ether were added and the mixture was washed three times with 55 ml potassium hydroxide solution (0.5 M) each time. The organic solution was extracted three times with 22 ml hydrochloric acid (5 wt. %) each time and the combined acid phases were washed with 10 ml ether and rendered alkaline (pH approx. 12) with 13 ml sodium hydroxide solution (32 wt. %). The mixture was extracted three times with 20 ml ether each time, the combined organic phases were dried over anhydrous magnesium sulfate and filtered and the filtrate was concentrated on a rotary evaporator (500–10 mbar). 1.72 g of crude base (97.6% of theory) were obtained and were introduced on to a 3×15 cm column packed with silica gel. Elution with ether/n-hexane 1:10 (v:v) gave 0.91 g of base. 0.39 g (45.5% of theory) N-(2'-dimethylaminomethyl-3-trifluoromethoxybiphenyl-4-yl)acetamide hydrochloride with a melting point of 182° C. was obtained from 0.40 g of this base according to example 1 (3rd stage) with chlorotrimethylsilane/water in 2-butanone.

Example 23
(3'-Isopropoxybiphenyl-2-ylmethyl)dimethylamine hydrochloride 1.51 g (7.31 mmol) of the dimethyl 2-(dimethylaminomethyl)-benzeneboronate prepared according to example 18 (1st stage), 1.05 g (4.87 mmol) 1-bromo-3-isopropoxybenzene and 1.72 g (16.2 mmol) sodium carbonate were dissolved in a mixture of 33 ml toluene, 13 ml water and 7 ml ethanol. 116 mg tetrakis (triphenylphosphine)palladium(0) were added under nitrogen and the mixture was heated under reflux (bath temperature 110° C.) for 16 hours.

For working up, 55 ml ether were added and the mixture was washed three times with 55 ml potassium hydroxide solution (0.5 M) each time. The organic solution was extracted three times with 22 ml hydrochloric acid (5 wt. %) each time and the combined acid phases were washed with 10 ml ether and rendered alkaline (pH approx. 12) with 13 ml sodium hydroxide solution (32 wt. %). The mixture was extracted three times with 20 ml ether each time, the combined organic phases were dried over anhydrous magnesium sulfate and filtered and the filtrate was concentrated on a rotary evaporator (500–10 mbar). 1.25 g of crude base (94.8% of theory) were obtained and were introduced on to a 3×15 cm column packed with silica gel. Elution with ether/n-hexane 1:20 (v:v) gave 0.65 g of base, from which 0.36 g (24.0% of theory) N-(2'-dimethylaminomethyl-3-trifluoromethoxybiphenyl-4-yl)acetamide hydrochloride was obtained according to example 1 (3rd stage) with chlorotrimethylsilane/water in 2-butanone.

Example 24
2'-(2-Dimethylaminoethyl)biphenyl-3-ol hydrochloride 0.89 g (3.49 mmol) of the base, prepared according to example 10 (2nd stage), of (3'-methoxybiphenyl-2-ylethyl) dimethylamine hydrochloride (10) were heated under reflux (bath temperature 145° C.) with 89 ml hydrogen bromide solution (48 wt. % in water) for two hours.

For working up, the mixture was poured into 1,000 ml sodium bicarbonate solution (1 M) (pH 7–8) and extracted four times with 100 ml ether each time, the combined organic extracts were dried over anhydrous magnesium sulfate and filtered and the filtrate was concentrated on a rotary evaporator (500 to 10 mbar). 0.32 g of crude base (38.5% of theory) was obtained, from which 0.26 g (27.9% of theory) 2'-(2-dimethylaminoethyl)biphenyl-3-ol hydrochloride with a melting point of 161° C. was obtained according to example 1 (3rd stage) with chlorotrimethylsilane/water in 2-butanone.

Example 25
4-Chloro-2'-dimethylaminomethylbiphenyl-3-ol hydrochloride 0.59 g (2.15 mmol) of the base, prepared according to example 21, of (4'-chloro-3'-methoxybiphenyl-2-ylmethyl) dimethylamine hydrochloride (21) were heated under reflux (bath temperature 145° C.) with 60 ml hydrogen bromide solution (48 wt. % in water) for two hours.

For working up, the mixture was poured in 140 ml water, brought to a pH of 7–8 by addition of solid sodium bicarbonate and extracted three times with 50 ml ether each time, the combined organic extracts were dried over anhydrous magnesium sulfate and filtered and the filtrate was concentrated on a rotary evaporator (500 to 10 mbar). 0.55 g of crude base (98.1% of theory) was obtained, from which 0.56 g (88.0% of theory) 4-chloro-2'-dimethylaminomethylbiphenyl-3-ol hydrochloride with a melting point of 194° C. was obtained according to example 1 (3rd stage) with chlorotrimethylsilane/water in 2-butanone.

Example 26
[2-(1H-Indol-5-yl)benzyl]dimethylamine 4.77 g (23.0 mmol) of the dimethyl 2-(dimethylaminomethyl)-benzeneboronate prepared according to example 18 (1st stage), 3.01 g (15.4 mmol) 5-bromoindole and 5.42 g (51.1 mmol) sodium carbonate were dissolved in a mixture of 105 ml toluene, 42 ml water and 21 ml ethanol. 364 mg tetrakis(triphenylphosphine) palladium(0) were added under nitrogen and the mixture was heated under reflux (bath temperature 110° C.) for 16 hours.

For working up, 100 ml ether were added and the mixture was washed three times with 100 ml potassium hydroxide solution (0.5 M) each time. The organic solution was extracted three times with 45 ml hydrochloric acid (5 wt. %) each time and the combined acid phases were washed with 20 ml ether and rendered alkaline (pH approx. 12) with 25 ml sodium hydroxide solution (32 wt. %). The mixture was extracted three times with 45 ml ether each time, the combined organic phases were dried over anhydrous magnesium sulfate and filtered and the filtrate was concentrated on a rotary evaporator (500–10 mbar). 2.23 g of crude base (58.1% of theory) were obtained and were introduced on to a 3×25 cm column packed with silica gel. Elution with ether/n-hexane 1:1 (v:v) gave 0.33 g (37.6% of theory) [2-(1H-indol-5-yl)benzyl]dimethylamine (37.6% of theory).

Example 27
(4'-Methanesulfonylbiphenyl-2-ylmethyl)dimethylamine hydrochloride 1.59 g (7.69 mmol) of the dimethyl 2-(dimethylaminomethyl)-benzeneboronate prepared according to example 18 (1st stage), 1.21 g (5.13 mmol)

4-bromophenyl methyl sulfone and 1.81 g (17.1 mmol) sodium carbonate were dissolved in a mixture of 35 ml toluene, 14 ml water and 7 ml ethanol. 122 mg tetrakis (triphenylphosphine)palladium(0) were added under nitrogen and the mixture was heated under reflux (bath temperature 110° C.) for 16 hours.

For working up, 55 ml ether were added and the mixture was washed three times with 55 ml potassium hydroxide solution (0.5 M) each time. The organic solution was extracted three times with 22 ml hydrochloric acid (5 wt. %) each time and the combined acid phases were washed with 10 ml ether and rendered alkaline (pH approx. 12) with 13 ml sodium hydroxide solution (32 wt. %). The mixture was extracted three times with 20 ml ether each time, the combined organic phases were dried over anhydrous magnesium sulfate and filtered and the filtrate was concentrated on a rotary evaporator (500–10 mbar). 0.67 g of crude base (55.3% of theory) was obtained and was introduced on to a 3×15 cm column packed with silica gel. Elution with ether/n-hexane 1:1 (v:v) gave 0.65 g of base, from which 0.62 g (37.2% of theory) (4'-methanesulfonylbiphenyl-2-ylmethyl) dimethylamine hydrochloride with a melting point of 173° C. was obtained according to example 1 (3rd stage) with chlorotrimethylsilane/water in 2-butanone.

Example 28

(2',4'-Dichlorobiphenyl-2-ylmethyl)dimethylamine hydrochloride 1.69 g (8.17 mmol) of the dimethyl 2-(dimethylaminomethyl)-benzeneboronate prepared according to example 18 (1st stage), 1.23 g (5.44 mmol) 2,4-dichlorobenzene bromide and 1.92 g (18.1 mmol) sodium carbonate were dissolved in a mixture of 37 ml toluene, 15 ml water and 8 ml ethanol. 129 mg tetrakis (triphenylphosphine)palladium(0) were added under nitrogen and the mixture was heated under reflux (bath temperature 110° C.) for 16 hours.

For working up, 60 ml ether were added and the mixture was washed three times with 60 ml potassium hydroxide solution (0.5 M) each time. The organic solution was extracted three times with 24 ml hydrochloric acid (5 wt. %) each time and the combined acid phases were washed with 10 ml ether and rendered alkaline (pH approx. 12) with 14 ml sodium hydroxide solution (32 wt. %). The mixture was extracted three times with 25 ml ether each time, the combined organic phases were dried over anhydrous magnesium sulfate and filtered and the filtrate was concentrated on a rotary evaporator (500–10 mbar). 0.62 g of crude base (40.3% of theory) was obtained and was introduced on to a 3×15 cm column packed with silica gel. Elution with ether/n-hexane 1:3 (v:v) gave 0.39 g of base, from which 0.25 g (15.2% of theory) (2',4'-dichlorobiphenyl-2-ylmethyl) dimethylamine hydrochloride with a melting point of 170–171° C. was obtained according to example 1 (3rd stage) with chlorotrimethylsilane/water in 2-butanone.

Example 29

(2',3'-Difluorobiphenyl-2-ylmethyl)dimethylamine hydrochloride 1.97 g (9.53 mmol) of the dimethyl 2-(dimethylaminomethyl)-benzeneboronate prepared according to example 18 (1st stage), 1.23 g (6.35 mmol) 2,3-difluorobenzene bromide and 2.24 g (21.2 mmol) sodium carbonate were dissolved in a mixture of 43 ml toluene, 17 ml water and 9 ml ethanol. 151 mg tetrakis (triphenylphosphine)palladium(0) were added under nitrogen and the mixture was heated under reflux (bath temperature 110° C.) for 16 hours.

For working up, 70 ml ether were added and the mixture was washed three times with 70 ml potassium hydroxide solution (0.5 M) each time. The organic solution was extracted three times with 27 ml hydrochloric acid (5 wt. %) each time and the combined acid phases were washed with 10 ml ether and rendered alkaline (pH approx. 12) with 16 ml sodium hydroxide solution (32 wt. %). The mixture was extracted three times with 30 ml ether each time, the combined organic phases were dried over anhydrous magnesium sulfate and filtered and the filtrate was concentrated on a rotary evaporator (500–10 mbar). 0.99 g of crude base (63.2% of theory) was obtained and was introduced on to a 3×15 cm column packed with silica gel. Elution with ether/n-hexane 1:3 (v:v) gave 0.61 g of base, from which 0.55 g (34.3% of theory) (2',3'-difluorobiphenyl-2-ylmethyl) dimethylamine hydrochloride with a melting point of 214° C. was obtained according to example 1 (3rd stage) with chlorotrimethylsilane/water in 2-butanone.

Example 30

(2',5'-Difluorobiphenyl-2-ylmethyl)dimethylamine hydrochloride 1.86 g (8.98 mmol) of the dimethyl 2-(dimethylaminomethyl)-benzeneboronate prepared according to example 18 (1st stage), 1.16 g (5.99 mmol) 2,5-difluorobenzene bromide and 2.11 g (19.9 mmol) sodium carbonate were dissolved in a mixture of 41 ml toluene, 17 ml water and 8 ml ethanol. 142 mg tetrakis (triphenylphosphine)palladium(0) were added under nitrogen and the mixture was heated under reflux (bath temperature 110° C.) for 16 hours.

For working up, 65 ml ether were added and the mixture was washed three times with 65 ml potassium hydroxide solution (0.5 M) each time. The organic solution was extracted three times with 26 ml hydrochloric acid (5 wt. %) each time and the combined acid phases were washed with 10 ml ether and rendered alkaline (pH approx. 12) with 15 ml sodium hydroxide solution (32 wt. %). The mixture was extracted three times with 25 ml ether each time, the combined organic phases were dried over anhydrous magnesium sulfate and filtered and the filtrate was concentrated on a rotary evaporator (500–10 mbar). 0.66 g of crude base (44.4% of theory) was obtained and was introduced on to a 3×15 cm column packed with silica gel. Elution with ether/n-hexane 1:3 (v:v) gave 0.40 g of base, from which 0.36 g (23.4% of theory) (2',5'-difluorobiphenyl-2-ylmethyl) dimethylamine hydrochloride with a melting point of 165° C. was obtained according to example 1 (3rd stage) with chlorotrimethylsilane/water in 2-butanone.

Example 31

(2-Benzo [1,3] dioxol-5-ylbenzyl)dimethylamine hydrochloride 1.71 g (8.24 mmol) of the dimethyl 2-(dimethylaminomethyl)-benzeneboronate prepared according to example 18 (1st stage), 1.10 g (5.49 mmol) 4-bromo-1,2-(methylenedioxy)benzene and 1.94 g (18.3 mmol) sodium carbonate were dissolved in a mixture of 38 ml toluene, 15 ml water and 8 ml ethanol. 130 mg tetrakis (triphenylphosphine)palladium(0) were added under nitrogen and the mixture was heated under reflux (bath temperature 110° C.) for 16 hours.

For working up, 55 ml ether were added and the mixture was washed three times with 55 ml potassium hydroxide solution (0.5 M) each time. The organic solution was extracted three times with 22 ml hydrochloric acid (5 wt. %) each time and the combined acid phases were washed with 10 ml ether and rendered alkaline (pH approx. 12) with 13 ml sodium hydroxide solution (32 wt. %). The mixture was extracted three times with 20 ml ether each time, the combined organic phases were dried over anhydrous magnesium sulfate and filtered and the filtrate was concentrated on a rotary evaporator (500–10 mbar). 1.46 g of crude base (104% of theory) were obtained and were introduced on to a 3×15 cm column packed with silica gel. Elution with ether/n-hexane 1:1 (v:v) gave 1.17 g of base, from which 1.20 g (74.8% of theory) (2-benzo[1,3]dioxol-5-ylbenzyl) dimethyl)amine hydrochloride with a melting point of 181° C. were obtained according to example 1 (3rd stage) with chlorotrimethylsilane/water in 2-butanone.

Example 32
1-[2'-(2-Dimethylaminoethyl)biphenyl-3-yl]ethanone hydrochloride 2.13 g (13.0 mol) 3-acetylbenzeneboronic acid, 1.98 g (8.68 mmol) [2-(2-bromophenyl)ethyl]dimethylamine prepared according to example 10 and 3.06 g (28.9 mmol) sodium carbonate were dissolved in a mixture of 60 ml toluene, 23 ml water and 12 ml ethanol. 206 mg tetrakis (triphenyl-phosphine)palladium(0) were added under nitrogen and the mixture was heated under reflux (bath temperature 110° C.) for 16 hours.

For working up, 90 ml ether were added and the mixture was washed three times with 90 ml potassium hydroxide solution (0.5 M) each time. The organic solution was extracted three times with 35 ml hydrochloric acid (5 wt. %) each time and the combined acid phases were washed with 20 ml ether and rendered alkaline (pH approx. 12) with 20 ml sodium hydroxide solution (32 wt. %). The mixture was extracted three times with 40 ml ether each time, the combined organic phases were dried over anhydrous magnesium sulfate and filtered and the filtrate was concentrated on a rotary evaporator (500–10 mbar). 2.08 g of crude base (89.5% of theory) were obtained, from which 1.57 g (59.6% of theory) 1-[2'-(2-dimethylaminoethyl)biphenyl-3-yl] ethanone hydrochloride with a melting point of 141° C. were obtained according to example 1 (3rd stage) with chlorotrimethylsilane/water in 2-butanone.

Example 33
[2-(3',4'-Dimethoxybiphenyl-2-yl)ethyl]dimethylamine hydrochloride 2.22 g (12.2 mmol) 3,4-dimethoxybenzeneboronic acid, 1.86 g (8.14 mmol) of the [2-(2-bromophenyl)ethyl] dimethylamine prepared according to example 10 and 2.87 g (27.1 mmol) sodium carbonate were dissolved in a mixture of 55 ml toluene, 22 ml water and 11 ml ethanol. 193 mg tetrakis(triphenylphosphine)palladium(0) were added under nitrogen and the mixture was heated under reflux (bath temperature 110° C.) for 16 hours.

For working up, 90 ml ether were added and the mixture was washed three times with 90 ml potassium hydroxide solution (0.5 M) each time. The organic solution was extracted three times with 35 ml hydrochloric acid (5 wt. %) each time and the combined acid phases were washed with 20 ml ether and rendered alkaline (pH approx. 12) with 20 ml sodium hydroxide solution (32 wt. %). The mixture was extracted three times with 35 ml ether each time, the combined organic phases were dried over anhydrous magnesium sulfate and filtered and the filtrate was concentrated on a rotary evaporator (500–10 mbar). 1.82 g of crude base (78.0% of theory) were obtained, from which 2.02 g (76.8% of theory) [2-(3',4'-dimethoxybiphenyl-2-yl)ethyl] dimethylamine hydrochloride with a melting point of 179° C. were obtained according to example 1 (3rd stage) with chlorotrimethylsilane/water in 2-butanone.

Example 34
[2-(3'-Isopropoxybiphenyl-2-yl)ethyl]dimethylamine hydrochloride

1st Stage
Dimethyl 2-(2-dimethylaminoethyl)benzeneboronate 19.0 g (83.2 mmol) of the [2-(2-bromophenyl)ethyl] dimethylamine prepared according to example 10 (2nd stage) were dissolved in 300 ml tetrahydrofuran and the solution was cooled to −70° C. in a cooling bath (isopropanol/dry ice). 60 ml (95.7 mmol) butyllithium solution (1.6 M in hexane) were added dropwise under nitrogen such that the temperature did not rise above −60° C. After the mixture had been stirred at −70° C. for two hours, 28 ml (250 mmol) trimethyl borate were also added dropwise such that the temperature did not rise above −60° C. The mixture was warmed to 25° C. in the course of 15 hours and the solution was concentrated on a rotary evaporator (500–10 mbar) without heat being supplied. The residue was taken up in 200 ml n-hexane, the mixture was stirred for one hour and filtered over an inert gas frit under nitrogen and the filtrated was concentrated on a rotary evaporator (500–10 mbar) without heat being supplied. 14.1 g dimethyl 2-(2-dimethylaminoethyl)benzeneboronate (76.5% of theory) were obtained in this manner.

2nd stage
[2-(3'-Isopropoxybiphenyl-2-yl)ethyl]dimethylamine hydrochloride 1.20 g (5.43 mmol) dimethyl 2-(dimethylaminoethyl) benzeneboronate from stage 1, 1.75 g (8.14 mmol) 3-bromoisopropoxybenzene and 1.92 g (18.1 mmol) sodium carbonate were dissolved in a mixture of 37 ml toluene, 15 ml water and 8 ml ethanol. 129 mg tetrakis (triphenylphosphine)palladium(0) were added under nitrogen and the mixture was heated under reflux (bath temperature 110° C.) for 16 hours.

For working up, 60 ml ether were added and the mixture was washed three times with 60 ml potassium hydroxide solution (0.5 M) each time. The organic solution was extracted three times with 23 ml hydrochloric acid (5 wt. %) each time and the combined acid phases were washed with 10 ml ether and rendered alkaline (pH approx. 12) with 14 ml sodium hydroxide solution (32 wt. %). The mixture was extracted three times with 25 ml ether each time, the combined organic phases were dried over anhydrous magnesium sulfate and filtered and the filtrate was concentrated on a rotary evaporator (500–10 mbar). 1.32 g of crude base (86.0% of theory) were obtained, from which 1.11 g (63.9% of theory) [2-(3'-isopropoxybiphenyl-2-yl)ethyl] dimethylamine hydrochloride with a melting point of 164° C. were obtained according to example 1 (3rd stage) with chlorotrimethylsilane/water in 2-butanone.

Example 35
[2-(4'-Chloro-3'-methoxybiphenyl-2-yl)ethyl] dimethylamine hydrochloride 1.20 g (5.43 mmol) of the dimethyl 2-(dimethylaminoethyl)-benzeneboronate prepared according to example 34 (1st stage), 1.80 g (8.14 mmol) 5-bromo-2-chloroanisole and 1.92 g (18.1 mmol) sodium carbonate were dissolved in a mixture of 37 ml toluene, 15 ml water and 8 ml ethanol. 129 mg tetrakis(triphenylphosphine) palladium(0) were added under nitrogen and the mixture was heated under reflux (bath temperature 110° C.) for 16 hours.

For working up, 60 ml ether were added and the mixture was washed three times with 60 ml potassium hydroxide solution (0.5 M) each time. The organic solution was extracted three times with 23 ml hydrochloric acid (5 wt. %)

each time and the combined acid phases were washed with 10 ml ether and rendered alkaline (pH approx. 12) with 14 ml sodium hydroxide solution (32 wt. %). The mixture was extracted three times with 25 ml ether each time, the combined organic phases were dried over anhydrous magnesium sulfate and filtered and the filtrate was concentrated on a rotary evaporator (500–10 mbar). 1.43 g of crude base (90.7% of theory) were obtained, from which 1.34 g (75.6% of theory) [2-(4'-chloro-3'-methoxybiphenyl-2-yl)ethyl] dimethylamine hydrochloride with a melting point of 227° C. were obtained according to example 1 (3rd stage) with chlorotrimethylsilane/water in 2-butanone.

Example 36

4-Chloro-2'-(2-dimethylaminoethyl)biphenyl-3-ol hydrochloride 0.58 g (2.01 mmol) of the base of the [2-(4'-chloro-3'-methoxybiphenyl-2-yl)ethyl]dimethylamine hydrochloride prepared according to example 35 were heated under reflux (bath temperature 145° C.) with 58 ml hydrogen bromide solution (48 wt. % in water) for two hours.

For working up, the mixture was poured into 700 ml sodium bicarbonate solution (1 M) (pH 7–8) and extracted three times with 100 ml ether each time, the combined organic extracts were dried over anhydrous magnesium sulfate and filtered and the filtrate was concentrated on a rotary evaporator (500 to 10 mbar). 0.54 g of crude base (98.0% of theory) was obtained, from which 0.51 g (93.5% of theory) 4-chloro-2'-(2-dimethylaminoethyl)biphenyl-3-ol hydrochloride with a melting point of 164° C. was obtained according to example 1 (3rd stage) with chlorotrimethylsilane/water in 2-butanone.

Example 37

Dimethyl-(3'-nitrobiphenyl-2-ylmethyl)amine hydrochloride 1.04 g (6.20 mmol) 3'-nitrobenzeneboronic acid, 1.21 g (5.64 mmol) of the (2-bromobenzyl)dimethylamine prepared according to example 1 (2nd stage) and 1.99 g (18.8 mmol) sodium carbonate were dissolved in a mixture of 40 ml toluene, 16 ml water and 8 ml ethanol. 134 mg tetrakis (triphenylphosphine)palladium(0) were added under nitrogen and the mixture was heated under reflux (bath temperature 110° C.) for 16 hours.

For working up, 65 ml ether were added and the mixture was washed three times with 65 ml potassium hydroxide solution (0.5 M) each time. The organic solution was extracted three times with 25 ml hydrochloric acid (5 wt. %) each time and the combined acid phases were washed with 10 ml ether and rendered alkaline (pH approx. 12) with 15 ml sodium hydroxide solution (32 wt. %). The mixture was extracted three times with 25 ml ether each time, the combined organic phases were dried over anhydrous magnesium sulfate and filtered and the filtrate was concentrated on a rotary evaporator (500–10 mbar). 714 mg of crude base (49.3% of theory) were obtained and were introduced on to a 3×25 cm column packed with silica gel. Elution with ether/n-hexane 1:3 (v:v) gave 330 mg of base, from which 262 mg (15.9% of theory) dimethyl-(3'-nitrobiphenyl-2-ylmethyl)amine hydrochloride with a melting point of 147° C. were obtained according to example 1 (3rd stage) with chlorotrimethylsilane/water in 2-butanone.

Example 38

4-Amino-2'-dimethylaminomethylbiphenyl-3-ol dihydrochloride 2.40 g (6.17 mmol) of the base of the N-(2'-dimethylaminomethyl-3-trifluoromethoxybiphenyl-4-yl) acetamide hydrochloride (22) prepared according to example 22 were heated under reflux (bath temperature 160° C.) with 110 ml hydrogen bromide solution (33 wt. % in glacial acetic acid) for six hours.

For working up, the mixture was poured into 1,000 ml ether and the supernatant was decanted off. The residue was dissolved in water, the solution was washed three times with 20 ml ether each time, brought to pH 7–8 with sodium bicarbonate solution (1 M) and extracted three times with 40 ml ether each time, the combined organic extracts were dried over anhydrous magnesium sulfate and filtered and the filtrate was concentrated on a rotary evaporator (500 to 10 mbar). 1.94 g of crude base (130% of theory) were obtained and were introduced on to a 3×30 cm column packed with silica gel. Elution with ether/n-hexane 2:1 (v:v) gave, in addition to 1.72 g of largely unchanged educt, 178 mg of crude base, from which 177 mg (7.5% of theory) 4-amino-2'-dimethylaminomethylbiphenyl-3-ol dihydrochloride, which decomposes on heating from 120° C., were obtained according to example 1 (3rd stage) with chlorotrimethylsilane/water in 2-butanone.

Example 39

(3',5'-Difluorobiphenyl-2-ylmethyl)dimethylamine hydrochloride 1.71 g (8.26 mmol) of the dimethyl 2-(dimethylaminomethyl)-benzeneboronate prepared according to example 18 (1st stage), 1.06 g (5.51 mmol) bromo-3,5-difluorobenzene and 1.94 g (18.3 mmol) sodium carbonate were dissolved in a mixture of 38 ml toluene, 15 ml water and 7.5 ml ethanol. 131 mg tetrakis (triphenylphosphine)palladium(0) were added under nitrogen and the mixture was heated under reflux (bath temperature 110° C.) for 16 hours.

For working up, 60 ml ether were added and the mixture was washed three times with 60 ml potassium hydroxide solution (0.5 M) each time. The organic solution was extracted three times with 24 ml hydrochloric acid (5 wt. %) each time and the combined acid phases were washed with 25 ml ether and rendered alkaline (pH approx. 12) with 14 ml sodium hydroxide solution (32 wt. %). The mixture was extracted three times with 25 ml ether each time, the combined organic phases were dried over anhydrous magnesium sulfate and filtered and the filtrate was concentrated on a rotary evaporator (500–10 mbar). 1.19 g of crude base (87.6% of theory) were obtained and were introduced on to a 3×25 cm column packed with silica gel. Elution with ether/n-hexane 1:3 (v:v) gave 990 mg of base, from which 1.06 g (37.2% of theory) (3',5'-difluorobiphenyl-2-ylmethyl) dimethylamine hydrochloride which decomposes on heating from 190° C. were obtained according to example 1 (3rd stage) with chlorotrimethylsilane/water in 2-butanone.

Example 40

(2',5'-Dimethoxybiphenyl-2-ylmethyl)dimethylamine hydrochloride 1.61 g (7.79 mmol) of the dimethyl 2-(dimethylaminomethyl)-benzeneboronate prepared according to example 18 (1st stage), 1.13 g (5.20 mmol) 2-bromo-1,4-dimethoxy-benzene and 1.83 g (17.3 mmol) sodium carbonate were dissolved in a mixture of 35 ml toluene, 14 ml water and 7 ml ethanol. 123 mg tetrakis (triphenylphosphine)palladium(0) were added under nitrogen and the mixture was heated under reflux (bath temperature 110° C.) for 16 hours.

For working up, 55 ml ether were added and the mixture was washed three times with 55 ml potassium hydroxide solution (0.5 M) each time. The organic solution was extracted three times with 22 ml hydrochloric acid (5 wt. %) each time and the combined acid phases were washed with 10 ml ether and rendered alkaline (pH approx. 12) with 13 ml sodium hydroxide solution (32 wt. %). The mixture was extracted three times with 20 ml ether each time, the combined organic phases were dried over anhydrous magnesium sulfate and filtered and the filtrate was concentrated on a rotary evaporator (500–10 mbar). 770 mg of crude base (61.0% of theory) were obtained, from which 777 mg (49.7% of theory) (2',5'-dimethoxybiphenyl-2-ylmethyl) dimethylamine hydrochloride with a melting point of 169° C. were obtained according to example 1 (3rd stage) with chlorotrimethylsilane/water in 2-butanone.

Example 41
2'-Dimethylaminomethyl-5-trifluoromethoxybiphenyl-2-ylamine dihydrochloride 6.24 g (30.1 mmol) of the dimethyl 2-(dimethylaminomethyl)-benzeneboronate prepared according to example 18 (1st stage), 5.14 g (20.1 mmol) 2-bromo-4-trifluoromethoxyphenylamine and 7.09 g (66.9 mmol) sodium carbonate were dissolved in a mixture of 140 ml toluene, 55 ml water and 27 ml ethanol. 476 mg tetrakis (triphenylphosphine)palladium(0) were added under nitrogen and the mixture was heated under reflux (bath temperature 110° C.) for 16 hours.

For working up, 220 ml ether were added and the mixture was washed three times with 220 ml potassium hydroxide solution (0.5 M) each time. The organic solution was extracted three times with 90 ml hydrochloric acid (5 wt. %) each time and the combined acid phases were washed with 90 ml ether and rendered alkaline (pH approx. 12) with 52 ml sodium hydroxide solution (32 wt. %). The mixture was extracted three times with 90 ml ether each time, the combined organic phases were dried over anhydrous magnesium sulfate and filtered and the filtrate was concentrated on a rotary evaporator (500–10 mbar). 3.46 g of crude base (55.5% of theory) were obtained and were introduced on to a 4×30 cm column packed with silica gel. Elution with ether/n-hexane 1:1 (v:v) gave 1.73 g of base (27.8% of theory). 389 mg 2'-dimethylaminomethyl-5-trifluoromethoxybiphenyl-2-ylamine dihydrochloride with a melting point of 125° C. were obtained from 316 mg of this base according to example 1 (3rd stage) with chlorotrimethylsilane/water in 2-butanone.

Example 42
N-(2'-Dimethylaminomethyl-5-trifluoromethoxybiphenyl-2-yl)acetamide hydrochloride 1.42 g (4.56 mmol) of the base of the 2'-dimethylaminomethyl-5-trifluoromethoxybiphenyl-2-ylamine prepared according to example 41 were heated (bath temperature 140° C.) with 80 ml hydrogen bromide solution (33 wt. % in glacial acetic acid) for 24 hours.

For working up, the mixture was poured into 800 ml ether and the supernatant was decanted off. The residue was dissolved in water, the solution was washed three times with 50 ml ether each time, rendered alkaline (pH>12) with potassium hydroxide solution (1 M) and extracted three times with 50 ml ether each time, the combined organic extracts were dried over anhydrous magnesium sulfate and filtered and the filtrate was concentrated on a rotary evaporator (500 to 10 mbar). 1.94 g of crude base (130% of theory) were obtained and were introduced on to a 3×30 cm column packed with silica gel. Elution with ether gave 940 mg of base (85.1% of theory). 274 mg N-(2'-dimethylaminomethyl-5-trifluoromethoxybiphenyl-2-yl) acetamide hydrochloride with a melting point of 115° C. were obtained from 303 mg of this base according to example 1 (3rd stage) with chlorotrimethylsilane/water in 2-butanone.

Example 43
3,5-Dichloro-2'-dimethylaminomethyl-biphenyl-4-ylamine hydrochloride 6.14 g (29.7 mmol) of the dimethyl 2-(dimethylaminomethyl)-benzeneboronate prepared according to example 18 (1st stage), 10.0 g (41.5 mmol) 4-bromo-2,6-dichloroaniline and 10.5 g (98.7 mmol) sodium carbonate were dissolved in a mixture of 100 ml toluene, 40 ml water and 20 ml ethanol. 354 mg tetrakis (triphenylphosphine)palladium(0) were added under nitrogen and the mixture was heated under reflux (bath temperature 110° C.) for 16 hours.

For working up, 200 ml ether were added and the mixture was washed three times with 130 ml potassium hydroxide solution (0.5 M) each time. The organic solution was extracted three times with 90 ml hydrochloric acid (5 wt. %) each time and the combined acid phases were washed with 50 ml ether and rendered alkaline (pH approx. 12) with 45 ml sodium hydroxide solution (32 wt. %). The mixture was extracted three times with 100 ml ether each time, the combined organic phases were dried over anhydrous magnesium sulfate and filtered and the filtrate was concentrated on a rotary evaporator (500–10 mbar). 6.88 g of crude base (78.7% of theory) were obtained. 470 mg (54.8% of theory) 3,5-dichloro-2'-dimethylaminomethylbiphenyl-4-ylamine hydrochloride were obtained from 765 mg of this crude product according to example 1 (3rd stage) with chlorotrimethylsilane/water in 2-butanone.

Pharmacological Studies
Writing Test in Mice

The analgesic activity was investigated on phenylquinone-induced writhing in mice (modified by I. C. Hendershot, J. Forsaith, J. Pharmacol. Exp. Ther. 125, 237–240 (1959)). Male NMRI mice weighing 25–30 g were used for this. Groups of 10 animals per dose of substance received 0.3 ml/mouse of a 0.02% aqueous solution of phenylquinone (phenylbenzoquinone, Sigma, Deisenhofen; preparation of the solution with addition of 5% ethanol and storage in a water bath at 45° C.) as an intraperitoneal administration 10 minutes after intravenous administration of the test substances. The animals were placed individually in observation cages. The number of pain-induced extension movements (so-called writhing reactions=straightening of the body with stretching out of the hind extremities) 5–20 minutes after the administration of phenylquinone was counted by means of a push-button counter. Animals which receive only physiological saline solution were also run as a control. All the substances were tested in the standard dosage of 10 mg/kg. The percentage inhibition (% inhibition) of the writhing reaction by a substance was calculated in accordance with the following equation:

$$\% \text{ inhibition} = 100 - \frac{\text{writhing reactions of treated animals}}{\text{writhing reactions of control animals}} \times 100$$

For some substances, the $ED_{50}$ values with 95% confidence limits of the writhing reaction were calculated from the dose-dependent decrease in the writhing reactions compared with phenylquinone control groups investigated in parallel by means of regression analysis (evaluation program of Martens EDV Service, Eckental Germany).

All the compounds according to the invention investigated showed a pronounced analgesic action. The results are summarized in the following table.

TABLE 1

Writhing test in mice

| Example | % Inhibition of the writhing reaction with 10 mg/kg intravenously | $ED_{50}$ (mg/kg intravenously) |
|---|---|---|
| (1) | 53 | |
| (2) | 89 | 4.55 |
| (3) | 100 | 0.24 |
| (4) | 75 | 3.95 |
| (5) | 68 | 4.31 |
| (6) | 88 | 4.26 |
| (7) | 90 | 2.55 |
| (8) | 67 | 7.15 |
| (9) | 89 | 2.32 |
| (10) | 100 | 1.70 |
| (11) | 74 | |
| (12) | 89 | 1.74 |
| (13) | 81 | 5.30 |
| (14) | 100 | 2.28 |
| (15) | 52 | 3.66 |
| (16) | 89 | 4.59 |
| (17) | 90 | |
| (18) | 83 | |
| (19) | 86 | |
| (20) | 83 | 4.99 |
| (21) | 53 | 6.78 |
| (22) | 76 | 6.05 |
| (23) | 97 | |
| (24) | 99 | 2.27 |
| (25) | 74 | |
| (26) | 100 | 0.75 |
| (27) | 89 | |
| (28) | 90 | |
| (29) | 83 | 5.71 |
| (30) | 89 | |
| (31) | 94 | |
| (32) | 98 | |
| (33) | 89 | |
| (34) | 80 | |
| (35) | 88 | |
| (36) | 93 | |
| (37) | 60 | |
| (38) | 65 | |
| (39) | 80 | |
| (40) | 57 | |
| (41) | 56 | |
| (42) | 44 | |
| (43) | 99 | |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A substituted 2-dialkylaminoalkylbiphenyl compound of formula I

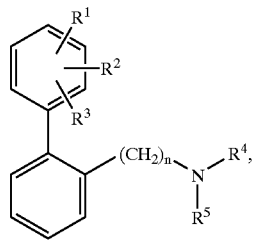

wherein n is 1 or 2;

$R^1$, $R^2$, $R^3$, which are identical or different, represent H, F, Cl, Br, CN, $NO_2$, CHO, $SO_2CH_3$, $SO_2CF_3$, $OR^6$ in the 3' or 5' position, $NR^6R^7$, a $C_{1-6}$-alkyl, an aryl, an acetyl, an acetamidyl or a benzoyl group or represent an aryl group bonded via a $C_{1-6}$-alkylene group;

or $R^1$ and $R^2$ together denote the group $OCH_2O$, $OCH_2CH_2O$, $CH=CHO$, $CH=C(CH_3)O$ or $CH=CHNH$;

$R^4$, $R^5$, which are identical or different, represent a $C_{1-6}$-alkyl group;

$R^6$, $R^7$, which are identical or different, represent H, a $C_{1-6}$-alkyl or an aryl group, or represent an aryl group bonded via a $C_{1-6}$-alkylene group;

or a physiologically tolerated salt, provided that the compounds:

2'-dimethylaminomethylbiphenyl-2-carbaldehyde;
biphenyl-2-ylmethyldimethylamine;
2'-dimethylaminomethylbiphenyl-2-ol, and the corresponding hydrochloride;
(2',3'-dimethoxybiphenyl-2-ylmethyl)dimethylamine, and the corresponding hydrochloride and hydrobromide;
(4'-methylbiphenyl-2-ylmethyl)-dimethylamine;
(2'-methylbiphenyl-2-ylmethyl)-dimethylamine;
(4)-chloro-2'-dimethylaminomethylbiphenyl-2-carbonitrile;
(2'-dimethylaminomethylbipheny-2-yl)methanol;
2'-dimethylaminomethylbiphenyl-2,3-diol, and the corresponding hydrobromide;
[2-(3',4'-dimethoxybiphenyl-2-yl)ethyl)]-dimethylamine, and the corresponding hydrochloride;
[2-(2', 3'-dimethoxy-6'-methylbiphenyl-2-yl)ethyl)]-dimethylamine, and the corresponding hydrobromide; and
biphenyl-2-ylethyldimethylamine are excluded.

2. A substituted 2-dialkylaminoalkylbiphenyl compound according to claim 1, wherein one or more of R1, R2 and R3 represent a $C_{1-3}$-alkyl group.

3. A substituted 2-dialkylaminoalkylbiphenyl compound according to claim 1, wherein one or more of $R^1$, $R^2$ and $R^3$ represent an aryl group bonded via a $C_{1-3}$-alkylene group.

4. A substituted 2-dialkylaminoalkylbiphenyl compound according to claim 1, wherein $R^4$ or $R^5$, or both, represent a $C_{1-3}$-alkyl group.

5. A substituted 2-dialkylaminoalkylbiphenyl compound according to claim 1, wherein $R^6$ or $R^7$, or both, represent a $C_{1-3}$-alkyl group.

6. A substituted 2-dialkylaminoalkylbiphenyl compound according to claim 1, wherein $R^6$ or $R^7$, or both, represent an aryl group bonded via a $C_{1-3}$alkylene group.

7. A substituted 2-dialkylaminoalkylbiphenyl compound selected from the group consisting of:

(3'-methoxybiphenyl-2-ylmethyl)dimethylamine and the corresponding hydrochloride;
(4'-chlorobiphenyl-2-ylmethyl)dimethylamine and the corresponding hydrochloride;
2'-dimethylaminomethylbiphenyl-3-ol and the corresponding hydrochloride;
(3'-chlorobiphenyl-2-ylmethyl)dimethylamine and the corresponding hydrochloride;
(2'-fluorobiphenyl-2-ylmethyl)dimethylamine and the corresponding hydrochloride;
(3'-fluorobiphenyl-2-ylmethyl)dimethylamine and the corresponding hydrochloride;
(4'-fluorobiphenyl-2-ylmethyl)dimethylamine and the corresponding hydrochloride;
(3'-chloro-4'-fluorobiphenyl-2-ylmethyl)dimethylamine and the corresponding hydrochloride;
(3'-methoxybiphenyl-2-ylethyl)dimethylamine and the corresponding hydrochloride;
dimethyl-[2-(2-methylbenzofuran-4-yl)benzyl]amine and the corresponding hydrochloride;
2'-dimethylaminomethylbiphenyl-2-carbaldehyde hydrochloride;
(3'-difluoromethylbiphenyl-2-ylmethyl)dimethylamine and the corresponding hydrochloride;
2'-dimethylaminomethylbiphenyl-3-carbaldehyde and the corresponding hydrochloride;
(3',4'-dichlorobiphenyl-2-ylmethyl)dimethylamine and the corresponding hydrochloride;
(3',5'-dichlorobiphenyl-2-ylmethyl)dimethylamine and the corresponding hydrochloride;
dimethyl-(4'-nitro-3'-trifluoromethylbiphenyl-2-ylmethyl)-amine and the corresponding hydrochloride;
(3',4'-difluorobiphenyl-2-ylmethyl)dimethylamine and the corresponding hydrochloride;
(4'-fluoro-3'-trifluoromethylbiphenyl-2-ylmethyl)dimethyl-amine and the corresponding hydrochloride;
(4'-chloro-3'-methoxybiphenyl-2-ylmethyl)dimethylamine and the corresponding hydrochloride;
N-(2'-dimethylaminomethyl-3-trifluoromethoxybiphenyl-4-yl)acetamide and the corresponding hydrochloride;
(3'-isopropoxybiphenyl-2-ylmethyl)dimethylamine and the corresponding and the corresponding hydrochloride;
2'-(2-dimethylaminoethyl)biphenyl-3-ol and the corresponding hydrochloride;
4-chloro-2'-dimethylaminomethylbiphenyl-3-ol and the corresponding hydrochloride;
[2-(1H-indol-5-yl)benzyl dimethylamine and the corresponding hydrochloride;
(4'-methanesulfonylbiphenyl-2-ylmethyl)dimethylamine and the corresponding hydrochloride;
(2',4'-dichlorobiphenyl-2-ylmethyl)dimethylamine and the corresponding hydrochloride;
(2',3'-difluorobiphenyl-2-ylmethyl)dimethylamine and the corresponding hydrochloride;
(2',5'-difluorobiphenyl-2-ylmethyl)dimethylamine and the corresponding hydrochloride;
(2-benzo[1,3]dioxol-5-ylbenzyl)dimethylamine and the corresponding hydrochloride;
1-2'-(2-dimethylaminoethyl)biphenyl-3-yl]ethanone and the corresponding hydrochloride;

[2-(3'-isopropoxybiphenyl-2-yl)ethyl]dimethylamine and the corresponding hydrochloride;
[2-(4'-chloro-3'-methoxybiphenyl-2-yl)ethyl]dimethylamine and the corresponding hydrochloride;
4-chloro-2'-(2-dimethylaminoethyl)biphenyl-3-ol and the corresponding hydrochloride;
dimethyl-(3'-nitrobiphenyl-2-ylmethyl)amine and the corresponding hydrochloride;
4-amino-2'-dimethylaminomethylbiphenyl-3-ol and the corresponding dihydrochloride;
(3',5'-difluorobiphenyl-2-ylmethyl)dimethylamine and the corresponding hydrochloride;
(2',5'-dimethoxybiphenyl-2-ylmethyl)dimethylamine and the corresponding hydrochloride;
2'-dimethylaminomethyl-5-trifluoromethoxybiphenyl-2-ylamine and the corresponding dihydrochloride;
N-(2'-dimethylaminomethyl-5-trifluoromethoxybiphenyl-2-yl)acetamide and the corresponding hydrochloride; and
3,5-dichloro-2'-dimethylaminomethyl-biphenyl-4-ylamine and the corresponding hydrochloride.

8. A process for the preparation of a substituted 2-dimethylaminoalkylbiphenyl compound of formula I,

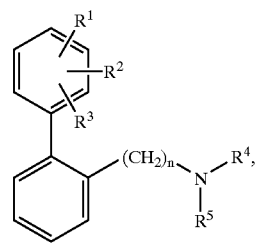

wherein
n is 1 or 2;
$R^1$, $R^2$, $R^3$, which are identical or different, represent H, F, Cl, Br, CN, $NO_2$, CHO, $SO_2CH_3$, $SO_2CF_3$, $OR^6$, $NR^6R^7$, a $C_{1-6}$-alkyl, an aryl, an acetyl, an acetamidyl or a benzoyl group or represent an aryl group bonded via a $C_{1-6}$-alkylene group;
or $R^1$ and $R^2$ together denote the group $OCH_2O$, $OCH_2CH_2O$, CH=CHO, CH=C(CH$_3$)O or CH=CHNH;
$R^4$, $R^5$, which are identical or different, represent H, or a $C_{1-6}$-alkyl group; and
$R^6$, $R^7$, which are identical or different, represent H, a $C_{1-6}$-alkyl or an aryl group, or represent an aryl group bonded via a $C_{1-6}$-alkylene group;
the process comprising:
(a) reducing a compound of formula II

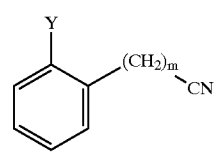

wherein Y denotes Cl, Br or I and m denotes 0 or 1, in solution with a first reducing agent to give rise to a compound of formula III,

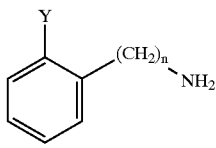

wherein n denotes 1 or 2, which is purified and isolated;

(b) reacting a compound of formula III with an aliphatic $C_{1-6}$-aldehyde in the presence of a second reducing agent to give rise to a compound of the general formula IV

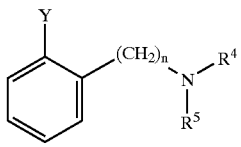

wherein $R^4$ and $R^5$ have the meaning according to formula I, which compound of formula IV is purified and isolated;

(c) converting a compound of formula IV by halogen-metal exchange and subsequent reaction with a boric acid ester at a temperature of $\leq 0°$ C. to give rise to a compound of formula V,

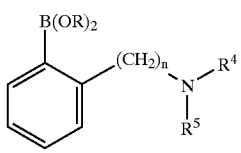

wherein R denotes an alkyl group;

(d) reacting a compound of formula V with an aqueous acid to give rise to a compound of formula VI

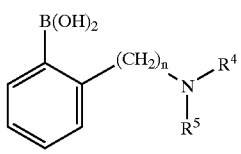

which is purified and isolated; and (e) reacting a compound of formula V or VI in a transition metal-catalysed reaction in an aliphatic ether, a hydrocarbon, an alcohol, a chlorinated hydrocarbon, water or mixtures thereof at a temperature between 20 and 150° C. with a compound of formula VII

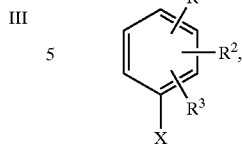

wherein X denotes Cl, Br, I or $OSO_2C_pF_{(2p+1)}$ and $R^1$, $R^2$, $R^3$, which are identical or different, represent H, F, Cl, Br, CN, $NO_2$, CHO, $SO_2CH_3$, $SO_2CF_3$, $OR^6$, $NR^6R^7$, a $C_{1-6}$-alkyl, an aryl, an acetyl, an acetamidyl or a benzoyl group or represent an aryl group bonded via a $C_{1-6}$-alkylene group;, to give rise to a compound of formula I, which is purified and isolated.

9. A process according to claim 8, wherein the compound of formula II is reduced with lithium aluminium hydride or diisobutylaluminium hydride, or both.

10. A process according to claim 8, wherein the compound of formula III is reacted with aliphatic $C_{1-6}$-aldehydes in the presence of formic acid, or sodium borohydride, or both.

11. A process according to claim 8, wherein the halogen-metal exchange is carried out with magnesium or butyllithium, or both.

12. A process according to claim 8, wherein the boric acid ester is a trialkyl borate.

13. The process of claim 12, wherein the trialkyl borate is trimethyl borate.

14. A process according to claim 8, wherein a compound of formula V is reacted with hydrochloric acid to give rise to a compound of formula VI.

15. A process according to claim 8, wherein a compound of formula V or VI is reacted in a reaction catalysed by palladium(0) compounds, or palladium(II) salts, or both.

16. A process according to claim 8, wherein the transition metal-catalysed reaction is carried out in 1,4-dioxane, tetrahydrofuran, toluene, hexane, ethanol, isopropanol, chloroform, methylene chloride, water or a mixture thereof.

17. The process of claim 8, wherein the compound of the general formula V in step (c) is optionally isolated and purified prior to reacting with an aqueous acid in step (d).

18. The process of claim 15, wherein the reaction is catalyzed by tetrakis(triphenylphosphine)palladium, bis(dibenzylideneacetone)palladium, elemental palladium on active charcoal, palladium(II) chloride or palladium(II) acetate, or mixtures thereof.

19. A pharmaceutical composition comprising, a substituted 2-dialkylaminoalkylbiphenyl compound of formula I

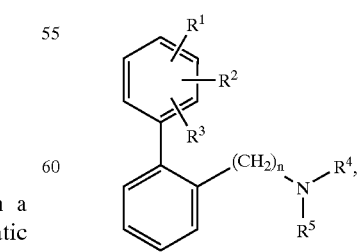

wherein n is 1 or 2;

R¹, R², R³, which are identical or different, represent H, F, Cl, Br, CN, $NO_2$, CHO, $SO_2CH_3$, $SO_2CF_3$, $OR^6$ in the 3' or 5' position, $NR^6R^7$, a $C_{1-6}$-alkyl, an aryl, an acetyl, an acetamidyl or a benzoyl group or represent an aryl group bonded via a $C_{1-6}$-alkylene group;

or R¹ and R² together denote the group $OCH_2O$, $OCH_2CH_2O$, CH=CHO, CH=C(CH₃)O or CH=CHNH;

R⁴, R⁵, which are identical or different, represent a $C_{1-6}$-alkyl group;

R⁶, R⁷, which are identical or different, represent H, a $C_{1-6}$-alkyl or an aryl group, or represent an aryl group bonded via a $C_{1-6}$-alkylene group;

or a physiologically tolerated salt thereof;

with the proviso that the compounds:
- 2'-dimethylaminomethylbiphenyl-2-carbaldehyde;
- biphenyl-2-ylmethyldimethylamine;
- 2'dimethylaminomethylbiphenyl-2-ol, and the corresponding hydrochloride;
- (2',3'dimethoxybiphenyl-2-ylmethyl)dimethylamine, and the corresponding hydrochloride and hydrobromide;
- (4'methylbiphenyl-2-ylmethyl)-dimethylamine
- (2'methylbiphenyl-2-ylmethyl)-dimethylamine
- 4-chloro-2'-dimethylaminomethylbiphenyl-2-carbonitrile;
- (2'dimethylaminomethylbiphenyl-2-yl)methanol;
- 2'-dimethylaminomethylbiphenyl-2,3-diol, and the corresponding hydrobromide;
- [2-(3',4'dimethoxybiphenyl-2-yl)ethyl)]-dimethylamine, and the corresponding hydrochloride;
- [2(2',3'-dimethoxy-6'-methylbiphenyl-2-yl)ethyl)]-dimethylamine, and the corresponding hydrobromide; and
- biphenyl-2-ylethyldimethylamine are excluded, and a pharmaceutically acceptable excipient.

20. A process according to claim 19, wherein a compound formula VIII or IX is reacted in a reaction catalysed by palladium(0) compounds or by palladium(II) salts, or both.

* * * * *